United States Patent
Yang et al.

(10) Patent No.: US 11,400,296 B2
(45) Date of Patent: *Aug. 2, 2022

(54) AV SYNCHRONOUS VFA CARDIAC THERAPY

(71) Applicant: Medtronic, Inc., Minneapolis, MN (US)

(72) Inventors: Zhongping Yang, Woodbury, MN (US); Thomas A. Anderson, New Hope, MN (US); Brian P. Colin, Shakopee, MN (US); William J. Clemens, Fridley, MN (US); Subham Ghosh, Blaine, MN (US); Jeffrey M. Gillberg, Coon Rapids, MN (US); Maurice T. I. Verbeek, Geleen (NL); Toine Camps, Eys Wittem (NL); Lilian Kornet, Maastricht (NL); Berthold Stegemann, Kassel (DE); Jean Rutten, Gulpen (NL)

(73) Assignee: Medtronic, Inc., Minneapolis, MN (US)

( * ) Notice: Subject to any disclaimer, the term of this patent is extended or adjusted under 35 U.S.C. 154(b) by 375 days.

This patent is subject to a terminal disclaimer.

(21) Appl. No.: 16/361,970

(22) Filed: Mar. 22, 2019

(65) Prior Publication Data

US 2019/0290910 A1   Sep. 26, 2019

Related U.S. Application Data

(60) Provisional application No. 62/647,426, filed on Mar. 23, 2018.

(51) Int. Cl.
*A61N 1/368* (2006.01)
*A61N 1/05* (2006.01)
(Continued)

(52) U.S. Cl.
CPC ......... *A61N 1/3684* (2013.01); *A61N 1/0573* (2013.01); *A61N 1/3627* (2013.01);
(Continued)

(58) Field of Classification Search
CPC .. A61N 1/0573; A61N 1/3627; A61N 1/3682; A61N 1/3684; A61N 1/371; A61N 1/37205; A61N 1/37518; A61N 1/3756
(Continued)

(56) References Cited

U.S. PATENT DOCUMENTS

| 3,835,864 A | 9/1974 | Rasor et al. |
| 3,865,118 A | 2/1975 | Bures |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Jonathan T Kuo
*Assistant Examiner* — Vynn V Huh

(57) ABSTRACT

VfA cardiac therapy uses an implantable medical device or system. The implantable medical device includes a tissue-piercing electrode implanted in the basal and/or septal region of the left ventricular myocardium of the patient's heart from the triangle of Koch region of the right atrium through the right atrial endocardium and central fibrous body. The device may include a right atrial electrode, a right atrial motion detector, or both. The device may be implanted completely within the patient's heart or may use one or more leads to implant electrodes in the patient's heart. The device may be used to provide cardiac therapy, including single or (Continued)

multiple chamber pacing, atrioventricular synchronous pacing, asynchronous pacing, triggered pacing, cardiac resynchronization pacing, or tachycardia-related therapy. A separate medical device may be used to provide some functionality for cardiac therapy, such as sensing, pacing, or shock therapy.

5 Claims, 23 Drawing Sheets

(51) Int. Cl.
    *A61N 1/362*     (2006.01)
    *A61N 1/372*     (2006.01)
    *A61N 1/375*     (2006.01)
    *A61N 1/37*     (2006.01)

(52) U.S. Cl.
    CPC ....... *A61N 1/3682* (2013.01); *A61N 1/37205* (2013.01); *A61N 1/37518* (2017.08); *A61N 1/371* (2013.01); *A61N 1/3756* (2013.01)

(58) Field of Classification Search
    USPC ........................................ 607/1–95, 115–156
    See application file for complete search history.

(56) References Cited

U.S. PATENT DOCUMENTS

| | | | |
|---|---|---|---|
| 3,943,936 A | 3/1976 | Rasor et al. |
| 3,949,757 A | 4/1976 | Sabel |
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Mass |
| 4,250,884 A | 2/1981 | Hartlaub et al. |
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,440,173 A | 4/1984 | Hudziak et al. |
| 4,476,868 A | 10/1984 | Thompson |
| 4,479,500 A | 10/1984 | Smits |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,574,814 A | 3/1986 | Buffet |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grievous et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon et al. |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |

(56) References Cited

U.S. PATENT DOCUMENTS

| | | |
|---|---|---|
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,623,518 B2 | 9/2003 | Thompson et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,754,528 B2 | 6/2004 | Bardy et al. |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |

(56) References Cited

U.S. PATENT DOCUMENTS

| | | |
|---|---|---|
| 6,804,558 B2 | 10/2004 | Haller et al. |
| 6,807,442 B1 | 10/2004 | Myklebust et al. |
| 6,847,844 B2 | 1/2005 | Sun et al. |
| 6,869,404 B2 | 3/2005 | Schulhauser et al. |
| 6,871,095 B2 | 3/2005 | Stahmann et al. |
| 6,871,096 B2 | 3/2005 | Hill |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,931,286 B2 | 8/2005 | Sigg et al. |
| 6,934,585 B1 | 8/2005 | Schloss et al. |
| 6,941,169 B2 | 9/2005 | Pappu |
| 6,957,107 B2 | 10/2005 | Rogers et al. |
| 6,978,176 B2 | 12/2005 | Lattouf |
| 6,980,675 B2 | 12/2005 | Evron et al. |
| 6,985,773 B2 | 1/2006 | Von Arx et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,035,684 B2 | 4/2006 | Lee et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,284 B2 | 2/2007 | Burnes et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |

(56) References Cited

U.S. PATENT DOCUMENTS

| | | |
|---|---|---|
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,209 B2 | 8/2011 | Jacobson |
| 8,014,861 B2 | 9/2011 | Zhu et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |

(56) References Cited

U.S. PATENT DOCUMENTS

| | | |
|---|---|---|
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,594,775 B2 | 11/2013 | Ghosh et al. |
| 8,612,002 B2 | 12/2013 | Faltys et al. |
| 8,615,310 B2 | 12/2013 | Khairkhahan et al. |
| 8,617,082 B2 | 12/2013 | Zhang et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,768,459 B2 | 7/2014 | Ghosh et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,861,830 B2 | 10/2014 | Brada et al. |
| 8,868,186 B2 | 10/2014 | Kroll |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,948,883 B2 | 2/2015 | Eggen et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,033,996 B1 | 5/2015 | West |
| 9,037,262 B2 | 5/2015 | Regnier et al. |
| 9,042,984 B2 | 5/2015 | Demmer et al. |
| 9,072,872 B2 | 7/2015 | Asleson et al. |
| 9,072,911 B2 | 7/2015 | Hastings et al. |
| 9,072,913 B2 | 7/2015 | Jacobson |
| 9,101,281 B2 | 8/2015 | Reinert et al. |
| 9,119,959 B2 | 9/2015 | Rys et al. |
| 9,155,882 B2 | 10/2015 | Grubac et al. |
| 9,168,372 B2 | 10/2015 | Fain |
| 9,168,380 B1 | 10/2015 | Greenhut et al. |

(56) References Cited

U.S. PATENT DOCUMENTS

| | | |
|---|---|---|
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashbili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,579,500 B2 | 2/2017 | Rys et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,789,319 B2 | 10/2017 | Sambelashvili |
| 9,808,628 B2 | 11/2017 | Sheldon et al. |
| 9,808,633 B2 | 11/2017 | Bonner et al. |
| 9,877,789 B2 | 1/2018 | Ghosh |
| 9,924,884 B2 | 3/2018 | Ghosh et al. |
| 10,004,467 B2 | 6/2018 | Lahm et al. |
| 10,064,567 B2 | 9/2018 | Ghosh et al. |
| 10,099,050 B2 | 10/2018 | Chen et al. |
| 10,166,396 B2 | 1/2019 | Schrock et al. |
| 10,251,555 B2 | 4/2019 | Ghosh et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0092995 A1 | 5/2003 | Thompson |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0064158 A1 | 4/2004 | Klein et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 12/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0008210 A1 | 1/2005 | Evron et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137629 A1 | 6/2005 | Dyjach et al. |
| 2005/0137671 A1 | 6/2005 | Liu et al. |

(56) References Cited

U.S. PATENT DOCUMENTS

| | | |
|---|---|---|
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288720 A1* | 12/2005 | Ross .............. A61N 1/3627 607/9 |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jaconson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0233216 A1 | 10/2007 | Liu et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0099619 A1 | 4/2009 | Lessmeier et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Jason |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0063375 A1 | 3/2010 | Kassab et al. |
| 2010/0063562 A1 | 3/2010 | Cowan et al. |
| 2010/0065871 A1 | 3/2010 | Govari et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0152798 A1 | 6/2010 | Sanghera et al. |
| 2010/0168761 A1 | 7/2010 | Kassab et al. |
| 2010/0168819 A1 | 7/2010 | Freeberg |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198304 A1 | 8/2010 | Wang |
| 2010/0217367 A1 | 8/2010 | Belson |
| 2010/0218147 A1 | 8/2010 | Ishikawa |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Ideblick et al. |
| 2011/0071586 A1 | 3/2011 | Jacobson |
| 2011/0077708 A1 | 3/2011 | Ostroff |
| 2011/0106202 A1 | 5/2011 | Ding et al. |
| 2011/0112398 A1 | 5/2011 | Zarkh et al. |

(56) References Cited

U.S. PATENT DOCUMENTS

| | | |
|---|---|---|
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0190841 A1 | 8/2011 | Sambelashvili et al. |
| 2011/0196444 A1 | 8/2011 | Prakash et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0035685 A1 | 2/2012 | Saha et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0089214 A1* | 4/2012 | Kroll ................ A61N 1/37 607/121 |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232478 A1 | 9/2012 | Haslinger |
| 2012/0232563 A1 | 9/2012 | Williams et al. |
| 2012/0232565 A1 | 9/2012 | Kveen et al. |
| 2012/0245665 A1 | 9/2012 | Friedman et al. |
| 2012/0263218 A1 | 10/2012 | Dal Molin et al. |
| 2012/0277600 A1 | 11/2012 | Greenhut |
| 2012/0277606 A1 | 11/2012 | Ellingson et al. |
| 2012/0277725 A1 | 11/2012 | Kassab et al. |
| 2012/0283587 A1 | 11/2012 | Gosh et al. |
| 2012/0283795 A1 | 11/2012 | Stancer et al. |
| 2012/0283807 A1 | 11/2012 | Deterre et al. |
| 2012/0284003 A1 | 11/2012 | Gosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0013017 A1 | 1/2013 | Mullen et al. |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053906 A1 | 2/2013 | Ghosh et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourg et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0131751 A1 | 5/2013 | Stadler et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0138006 A1 | 11/2013 | Bornzin et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0339570 A1 | 2/2014 | Carroll et al. |
| 2014/0074114 A1 | 3/2014 | Khairkhahan et al. |

(56) References Cited

U.S. PATENT DOCUMENTS

| | | |
|---|---|---|
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1* | 4/2014 | Hou .................. A61N 1/3756 607/28 |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0330208 A1 | 11/2014 | Christie et al. |
| 2014/0330287 A1 | 11/2014 | Thompson-Naumann et al. |
| 2014/0336326 A1 | 11/2014 | Thompson-Naumann et al. |
| 2014/0358135 A1 | 12/2014 | Sambelashvili et al. |
| 2014/0371832 A1 | 12/2014 | Ghosh |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0305695 A1 | 10/2015 | Lahm et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335894 A1 | 11/2015 | Bornzin et al. |
| 2016/0015287 A1 | 1/2016 | Anderson et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0045738 A1 | 2/2016 | Ghosh et al. |
| 2016/0051821 A1 | 2/2016 | Sambelashvili et al. |
| 2016/0059002 A1 | 3/2016 | Grubac et al. |
| 2016/0067486 A1 | 3/2016 | Brown et al. |
| 2016/0067487 A1 | 3/2016 | Demmer et al. |
| 2016/0067490 A1 | 3/2016 | Carney et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129239 A1 | 5/2016 | Anderson |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0310733 A1 | 10/2016 | Sheldon et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056670 A1 | 3/2017 | Sheldon et al. |
| 2017/0182327 A1 | 6/2017 | Liu |
| 2017/0189681 A1 | 7/2017 | Anderson |
| 2017/0209689 A1 | 7/2017 | Chen |
| 2017/0216575 A1 | 8/2017 | Asleson et al. |
| 2017/0304624 A1 | 10/2017 | Friedman et al. |
| 2017/0326369 A1 | 11/2017 | Koop et al. |
| 2017/0340885 A1 | 11/2017 | Sambelashvili |
| 2018/0008829 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140848 A1 | 5/2018 | Stahmann |
| 2018/0178007 A1 | 6/2018 | Shuros et al. |
| 2018/0212451 A1 | 7/2018 | Schmidt et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0280686 A1 | 10/2018 | Shuros et al. |
| 2018/0326215 A1 | 11/2018 | Ghosh |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |

(56) References Cited

U.S. PATENT DOCUMENTS

| | | | |
|---|---|---|---|
| 2019/0192860 A1 | 6/2019 | Ghosh et al. | |
| 2019/0269926 A1 | 9/2019 | Ghosh | |

FOREIGN PATENT DOCUMENTS

| | | |
|---|---|---|
| AU | 2014203793 A1 | 7/2014 |
| CN | 202933393 | 5/2013 |
| EP | 0362611 A1 | 4/1990 |
| EP | 0459 239 A2 | 12/1991 |
| EP | 0 728 497 A2 | 8/1996 |
| EP | 1 541 191 A1 | 6/2005 |
| EP | 1 702 648 A1 | 9/2006 |
| EP | 1 904 166 B1 | 6/2011 |
| EP | 2 452 721 A1 | 5/2012 |
| EP | 2 471 452 A1 | 7/2012 |
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 02/22206 | 3/2002 |
| WO | WO 03/092800 | 11/2003 |
| WO | WO 2005/000206 A2 | 1/2005 |
| WO | WO 2005/042089 A1 | 5/2005 |
| WO | WO 2006/086435 A2 | 8/2006 |
| WO | WO 2006/113659 A1 | 10/2006 |
| WO | WO 2007/073435 A1 | 6/2007 |
| WO | WO 2007/075974 A2 | 7/2007 |
| WO | WO 2009/006531 A1 | 1/2009 |
| WO | WO 2013/080038 A2 | 6/2013 |
| WO | WO 2013/098644 A2 | 7/2013 |
| WO | WO 2015/081221 A1 | 6/2015 |
| WO | WO 2016/011042 A1 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | WO 2018/009569 A1 | 1/2018 |
| WO | WO 2018/017226 A1 | 1/2018 |
| WO | WO 2018/017361 A1 | 1/2018 |
| WO | WO 2018/035343 A1 | 2/2018 |
| WO | WO 2018/081519 A1 | 5/2018 |

OTHER PUBLICATIONS

International Preliminary Report on Patentability from PCT Application No. PCT/US2019/023636 dated Oct. 8, 2020, 9 pages.
International Preliminary Report on Patentability from PCT Application No. PCT/US2019/023642 dated Oct. 8, 2020, 9 pages.
International Preliminary Report on Patentability from PCT Application No. PCT/US2019/023645 dated Oct. 8, 2020, 7 pages.
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.
Stroobandt et al., "Prediction of Wenckebach Behavior and Block Response in DDD Pacemakers," *Pacing Clin Electrophysiol.*, Jun. 2006; 9(6):1040-6.
Suenari et al., "Idiopathic left ventricular tachycardia with dual electrocardiogram morphologies in a single patient," *Europace*, Apr. 2010; 12(4):592-4.
Sweeney et al., "Analysis of Ventricular Activation Using Surface Electrocardiography to Predict Left Ventricular Reverse Volumetric Remodeling During Cardiac Resynchronization Therapy," Circulation, Feb. 9, 2010, 121(5): 626-34.
Tan et al., "Electrocardiographic evidence of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide and Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: A Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007; 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004, 6(5):433-7.

(56) References Cited

OTHER PUBLICATIONS

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His-bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.
Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Violi et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non-coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.

Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000; 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short- and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.
(PCT/US2014/036782) PCT Notification of Transmittal of the International Search Report and the Written Opinion of the International Searching Authority, dated Aug. 22, 2014, 11 pages.
International Search Report and Written Opinion for Application No. PCT/US2017/047378, 8 pages, dated Dec. 6, 2017.
(PCT/US2018/050988) PCT Notification of Transmittal of the International Search Report and the Written Opinion of the International Searching Authority, dated Nov. 14, 2018, 11 pages.
(PCT/US2018/050993) PCT Notification of Transmittal of the International Search Report and the Written Opinion of the International Searching Authority, dated Nov. 16, 2018, 7 pages.
(PCT/US2019/023642) PCT Notification of Transmittal of the International Search Report and the Written Opinion of the International Searching Authority, dated Jun. 28, 2019, 14 pages.
http://www.isrctn.com/ISRCTN47824547, public posting published Aug. 2019.
Abed et al., "Obesity results in progressive atrial structural and electrical remodeling: Implications for atrial fibrillation," *Heart Rhythm Society*, Jan. 2013; 10(1):90-100.
Adragão et al., "Ablation of pulmonary vein foci for the treatment of atrial fibrillation; percutaneous electroanatomical guided approach," *Europace*, Oct. 2002; 4(4):391-9.
Aliot et al., "Arrhythmia detection by dual-chamber implantable cardioverter defibrillators: A review of current algorithms," *Europace*, Jul. 2004; 6(4):273-86.
Amirahmadi et al., "Ventricular Tachycardia Caused by Mesothelial Cyst," *Indian Pacing and Electrophysiology Journal*, 2013; 13(1):43-44.
Ammirabile et al., "Pitx2 confers left morphological, molecular, and functional identity to the sinus venosus myocardium," *Cardiovasc Res.*, Feb. 2012; 93(2):291-301.
Anfinsen, "Non-pharmacological Treatment of Atrial Fibrillation," *Indian Pacing and Electrophysiology Journal*, Jan. 2002; 2(1):4-14.
Anné et al., "Ablation of post-surgical intra-atrial reentrant Tachycardia," *European Heart Journal*, 2002; 23:169-1616.

(56) References Cited

OTHER PUBLICATIONS

Arenal et al., "Dominant frequency differences in atrial fibrillation patients with and without left ventricular systolic dysfunction," *Europace*, Apr. 2009; 11(4):450-457.
Arriagada et al., "Predictors of arrhythmia recurrence in patients with lone atrial fibrillation," *Europace*, Jan. 2008; 10(1):9-14.
Asirvatham et al., "Cardiac Anatomic Considerations in Pediatric Electrophysiology," *Indian Pacing and Electrophysiology Journal*, Apr. 2008; 8(Suppl 1):S75-S91.
Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.
Asirvatham et al., "Letter to the Editor," *J Cardiovasc Electrophysiol.*, Mar. 2010; 21(3): E77.
Balmer et al., "Long-term follow up of children with congenital complete atrioventricular block and the impact of pacemaker therapy," *Europace*, Oct. 2002; 4(4):345-349.
Barold et al., "Conventional and biventricular pacing in patients with first-degree atrioventricular block," *Europace*, Oct. 2012; 14(10):1414-9.
Barold et al., "The effect of hyperkalaemia on cardiac rhythm devices," *Europace*, Apr. 2014; 16(4):467-76.
Bayrak et al., "Added value of transoesophageal echocardiography during transseptal puncture performed by inexperienced operators," *Europace*, May 2012; 14(5):661-5.
Bergau et al., "Measurement of Left Atrial Pressure is a Good Predictor of Freedom From Atrial Fibrillation," *Indian Pacing and Electrophysiology Journal*, Jul. 2014; 14(4):181-93.
Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.
Bito et al., "Early exercise training after myocardial infarction prevents contractile but not electrical remodeling or hypertrophy," *Cardiovascular Research*, Apr. 2010; 86(1):72-81.
Bollmann et al., "Analysis of surface electrocardiograms in atrial fibrillation: techniques, research, and clinical applications," *Europace*, Nov. 2006; 8(11):911-926.
Bortone et al., "Evidence for an incomplete mitral isthmus block after failed ablation of a left postero-inferior concealed accessory pathway," *Europace*, Jun. 2006; 8(6):434-7.
Boulos et al., "Electroanatomical mapping and radiofrequency ablation of an accessory pathway associated with a large aneurysm of the coronary sinus," *Europace*, Nov. 2004; 6(6):608-12.
Brembilla-Perrot et al., "Incidence and prognostic significance of spontaneous and inducible antidromic tachycardia," *Europace*, Jun. 2013; 15(6):871-876.
Buber et al., "Morphological features of the P-waves at surface electrocardiogram as surrogate to mechanical function of the left atrium following a successful modified maze procedure," *Europace*, Apr. 2014; 16(4):578-86.
Burashnikov et al., "Late-phase 3 EAD. A unique mechanism contributing to initiation of atrial fibrillation," *Pacing Clin Electrophysiol.*, Mar. 2006; 29(3):290-5.
Burashnikov et al., "Atrial-selective inhibition of sodium-channel current by Wenxin Keli is effective in suppressing atrial fibrillation," *Heart Rhythm*, Jan. 2012; 9(1):125-31.
Calvo et al., "Efficacy of circumferential pulmonary vein ablation of atrial fibrillation in endurance athletes," *Europace*, Jan. 2010; 12(1):30-6.
Can et al., ""Atrial torsades de pointes" Induced by Low-Energy Shock From Implantable-Cardioverter Defibrillator," *Indian Pacing and Electrophysiology Journal*, Sep. 2013; 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.
Cazeau et al., "Cardiac resynchronization therapy," *Europace*, Sep. 2004; 5 Suppl 1:S42-8.
Chandra et al., "Evaluation of KCB-328, a new IKr blocking antiarrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4):142-7.
Climent et al., "Effects of endocardial microwave energy ablation," *Indian Pacing and Electrophysiology Journal*, Jul. 2005; 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*,1998, 193:105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *Pace*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.
Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.

(56) References Cited

OTHER PUBLICATIONS

Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2):189-91.
Guillem et al., "Noninvasive mapping of human atrial fibrillation," *J Cardiovasc Electrophysiol.*, May 2009; 20(5):507-513.
Hachisuka et al., "Development and Performance Analysis of an Intra-Body Communication Device," The $12^{th}$ International Conference on Solid State Sensors, Actuators and Microsystems, vol. 4A1.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8):1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus—Preliminary Results," *J Cardiovasc Electrophysiol.*, Dec. 2009; 20(12):1391-1397.
Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.
Inter-Office Memo, Model 6426-85 Canine Feasibility AV Septal 8 mm Screw-In Right Single Pass DDD Lead Final Report (AR # 0120A0207).
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.

Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.
Kalbfleisch et al., "Catheter Ablation with Radiofrequency Energy: Biophysical Aspects and Clinical Applications," *Journal of Cardiovascular Electrophysiology*, Oct. 2008; 3(2):173-186.
Katritsis et al., "Classification and differential diagnosis of atrioventricular nodal re-entrant tachycardia," *Europace*, Jan. 2006; 8(1):29-36.
Katritsis et al., "Anatomically left-sided septal slow pathway ablation in dextrocardia and situs inversus totalis," *Europace*, Aug. 2008; 10(8):1004-5.
Khairy et al., "Cardiac Arrhythmias in Congenital Heart Diseases," *Indian Pacing and Electrophysiology Journal*, Nov.-Dec. 2009; 9(6):299-317.
Kimmel et al., "Single-site ventricular and biventricular pacing: investigation of latest depolarization strategy," *Europace*, Dec. 2007; 9(12):1163-1170.
Knackstedt et al., "Electro-anatomic mapping systems in arrhythmias," *Europace*, Nov. 2008; 10 Suppl 3:iii28-iii34.
Kobayashi et al., "Successful Ablation of Antero-septal Accessory Pathway in the Non-Coronary Cusp in a Child," *Indian Pacing and Electrophysiology Journal*, 2012; 12(3):124-130.
Kojodjojo et al., "4:2:1 conduction of an AF initiating trigger," *Indian Pacing and Electrophysiology Journal*, Nov. 2015; 15(5):255-8.
Kołodzińska et al., "Differences in encapsulating lead tissue in patients who underwent transvenous lead removal," *Europace*, Jul. 2012; 14(7):994-1001.
Konecny et al., "Synchronous intra-myocardial ventricular pacing without crossing the tricuspid valve or entering the coronary sinus," *Cardiovascular Revascularization Medicine*, 2013; 14:137-138.
Kriatselis et al., "Ectopic atrial tachycardias with early activation at His site: radiofrequency ablation through a retrograde approach," *Europace*, Jun. 2008; 10(6):698-704.
Lalu et al., "Ischaemia-reperfusion injury activates matrix metalloproteinases in the human heart," *Eur Heart J.*, Jan. 2005; 26(1):27-35.
Laske et al., "Excitation of the Intrinsic Conduction System Through His and Interventricular Septal Pacing," *Pacing Clin. Electrophysiol.*, Apr. 2006; 29(4):397-405.
Leclercq, "Problems and troubleshooting in regular follow-up of patients with cardiac resynchronization therapy," *Europace*, Nov. 2009; 11 Suppl 5:v66-71.
Lee et al., "An unusual atrial tachycardia in a patient with Friedreich ataxia," *Europace*, Nov. 2011; 13(11):1660-1.
Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.
Lemay et al., "Spatial dynamics of atrial activity assessed by the vectorcardiogram: from sinus rhythm to atrial fibrillation," *Europace*, Nov. 2007; 9 Suppl 6:vi109-18.
Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.
Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.
Liakopoulos et al., "Sequential deformation and physiological considerations in unipolar right and left ventricular pacing," *European Journal of Cardio-thoracic Surgery*, Apr. 1, 2006; 29S1:S188-197.
Lian et al., "Computer modeling of ventricular rhythm during atrial fibrillation and ventricular pacing," *IEEE Transactions on Biomedical Engineering*, Aug. 2006; 53(8):1512-1520.
Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.

(56) References Cited

OTHER PUBLICATIONS

Lim et al., "Coupled pacing improves left ventricular function during simulated atrial fibrillation without mechanical dyssynchrony," *Europace*, Mar. 2010; 12(3):430-6.

Lou et al., "Tachy-brady arrhythmias: The critical role of adenosine-induced sinoatrial conduction block in post-tachycardia pauses," *Heart Rhythm.*, Jan. 2013; 10(1):110-8.

Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.

Macedo et al, "Septal accessory pathway: anatomy, causes for difficulty, and an approach to ablation," *Indian Pacing and Electrophysiology Journal*, Jul. 2010; 10(7):292-309.

Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.

Mani et al., "Dual Atrioventricular Nodal Pathways Physiology: A Review of Relevant Anatomy, Electrophysiology, and Electrocardiographic Manifestations," *Indian Pacing and Electrophysiology Journal*, Jan. 2014; 14(1):12-25.

Manios et al., "Effects of successful cardioversion of persistent atrial fibrillation on right ventricular refractoriness and repolarization," *Europace*, Jan. 2005; 7(1):34-9.

Manolis et al., "Prevention of atrial fibrillation by inter-atrial septum pacing guided by electrophysiological testing, in patients with delayed interatrial conduction," *Europace*, Apr. 2002; 4(2):165-174.

Marino et al., "Inappropriate mode switching clarified by using a chest radiograph," *Journal of Arrhythmia*, Aug. 2015; 31(4):246-248.

Markowitz et al., "Time course and predictors of autonomic dysfunction after ablation of the slow atrioventricular nodal pathway," *Pacing Clin Electrophysiol.*, Dec. 2004; 27(12):1638-43.

Marshall et al., "The effects of temperature on cardiac pacing thresholds," *Pacing Clin Electrophysiol.*, Jul. 2010; 33(7):826-833.

McSharry et al., "A Dynamical Model for Generating Synthetic Electrocardiogram Signals," *IEEE Transactions on Biomedical Engineering*, Mar. 2003; 50(3):289-294.

Meijler et al., "Scaling of Atrioventricular Transmission in Mammalian Species: An Evolutionary Riddle!," *Journal of Cfardiovascular Electrophysiology*, Aug. 2002; 13(8):826-830.

Meiltz et al., "Permanent form of junctional reciprocating tachycardia in adults: peculiar features and results of radiofrequency catheter ablation," *Europace*, Jan. 2006; 8(1):21-8.

Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.

Mestan et al., "The influence of fluid and diuretic administration on the index of atrial contribution in sequentially paced patients," *Europace*, Apr. 2006; 8(4):273-8.

Metin et al., "Assessment of the P Wave Dispersion and Duration in Elite Women Basketball Players," *Indian Pacing and Electrophysiology Journal*, 2010; 10(1):11-20.

Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.

Mitchell et al., "How do atrial pacing algorithms prevent atrial arrhythmias?" *Europace*, Jul. 2004; 6(4):351-62.

Mirzoyev et al., "Embryology of the Conduction System for the Electrophysiologist," *Indian Pacing and Electrophysiology Journal*, 2010; 10(8):329-338.

Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.

Montgomery et al., "Measurement of diffuse ventricular fibrosis with myocardial T1 in patients with atrial fibrillation," *J Arrhythm.*, Feb. 2016; 32(1):51-6.

Mulpuru et al., "Synchronous ventricular pacing with direct capture of the atrioventricular conduction system: Functional anatomy, terminology, and challenges," *Heart Rhythm*, Nov. 2016; Epub Aug. 3, 2016; 13(11):2237-2246.

Musa et al., "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.

Nagy et al., "Wnt-11 signalling controls ventricular myocardium development by patterning N-cadherin and β-catenin expression," *Cardiovascular Research*, Jan. 2010; 85(1):100-9.

Namboodiri et al., "Electrophysiological features of atrial flutter in cardiac sarcoidosis: a report of two cases," *Indian Pacing and Electrophysiology Journal*, Nov. 2012; 12(6):284-9.

Nanthakumar et al., "Assessment of accessory pathway and atrial refractoriness by transesophageal and intracardiac atrial stimulation: An analysis of methodological agreement," *Europace*, Jan. 1999; 1(1):55-62.

Neto et al., "Temporary atrial pacing in the prevention of postoperative atrial fibrillation," *Pacing Clin Electrophysiol.*, Jan. 2007; 30(Suppl 1):S79-83.

Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.

Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.

Okumura et al., "Effects of a high-fat diet on the electrical properties of porcine atria," *Journal of Arrhythmia*, Dec. 2015; 31(6):352-358.

Olesen et al., "Mutations in sodium channel β-subunit SCN3B are associated with early-onset lone atrial fibrillation," *Cardiovascular Research*, Mar. 2011; 89(4):786-93.

Ozmen et al., "P wave dispersion is increased in pulmonary stenosis," *Indian Pacing and Electrophysiology Journal*, Jan. 2006; 6(1):25-30.

Packer et al., "New generation of electro-anatomic mapping: Full intracardiac image integration," *Europace*, Nov. 2008; 10 Suppl 3:iii35-41.

Page et al., "Ischemic ventricular tachycardia presenting as a narrow complex tachycardia," *Indian Pacing and Electrophysiology Journal*, Jul. 2014; 14(4):203-210.

Pakarinen et al., "Pre-implant determinants of adequate long-term function of single lead VDD pacemakers," *Europace*, Apr. 2002; 4:137-141.

Patel et al., "Atrial Fibrillation after Cardiac Surgery: Where are we now?" *Indian Pacing and Electrophysiology Journal*, Oct.-Dec. 2008; 8(4):281-291.

Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.

Peschar et al., "Left Ventricular Septal and Apex Pacing for Optimal Pump Function in Canine Hearts," *J Am Coll Cardiol.*, Apr. 2, 2003; 41(7):1218-1226.

Physiological Research Laboratories, Final Report for an Acute Study for Model 6426-85 AV Septal Leads, Feb. 1996.

Porciani et al., "Interatrial septum pacing avoids the adverse effect of interatrial delay in biventricular pacing: an echo-Doppler evaluation," *Europace*, Jul. 2002; 4(3):317-324.

Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.

Prystowsky et al., "Case studies with the experts: management decisions in atrial fibrillation," *J Cardiovasc Electrophysiol.*, Feb. 2008; 19(Suppl. 1):S1-12.

Prystowsky, "The history of atrial fibrillation: the last 100 years," *J Cardiovasc Electrophysiol*, Jun. 2008; 19(6):575-582.

(56) References Cited

OTHER PUBLICATIONS

Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12):1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology Journal*, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated DENSE strain imaging for post-radiofrequency ablation lesion assessment in the swine left atria," *Europace*, Jan. 2014; 16(1):133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.

\* cited by examiner

AV SYNCHRONOUS VFA CARDIAC THERAPY

The present application claims the benefit of U.S. Provisional Application Ser. No. 62/647,426, filed Mar. 23, 2018, which is incorporated herein by reference in its entirety.

The present disclosure relates to implantable medical devices, systems, and methods. In particular, the present disclosure relates to implantable medical devices, systems, and methods for ventricle-from-atrium (VfA) cardiac therapy, including single chamber or multiple chamber pacing (e.g., dual or triple chamber pacing), atrioventricular synchronous pacing, asynchronous pacing, triggered pacing, cardiac resynchronization pacing, or tachycardia-related therapy.

The cardiac conduction system includes the sinus atrial (SA) node, the atrioventricular (AV) node, the bundle of His, bundle branches and Purkinje fibers. A heart beat is initiated in the SA node, which may be described as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in different ventricles of the heart. Significant differences in timing of contractions can reduce cardiac efficiency. CRT, delivered by an IMD to the heart, may enhance cardiac output by resynchronizing the electromechanical activity of the ventricles of the heart. CRT is sometimes referred to as "triple chamber pacing" because of pacing the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP), a painless therapy, can be used to treat ventricular tachycardia (VT) to substantially terminate many monomorphic fast rhythms. While ATP is painless, ATP may not deliver effective therapy for all types of VTs. For example, ATP may not be as effective for polymorphic VTs, which has variable morphologies. Polymorphic VTs and ventricular fibrillation (VFs) can be more lethal and may require expeditious treatment by shock.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single chamber of the patient's heart. Single chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

In some patients, single chamber devices may adequately address the patient's needs. However, single chamber devices capable of only single chamber sensing and therapy may not fully address cardiac conduction disease or abnormalities in all patients, for example, those with some forms of AV dyssynchrony or tachycardia. Dual chamber sensing and/or pacing functions, in addition to ICD functionality in some cases, may be used to restore more normal heart rhythms.

SUMMARY

Various embodiments of the present disclosure relate to implantable medical devices, systems, and methods for VfA cardiac therapy, including single or multiple chamber pacing (e.g., dual or triple chamber pacing), atrioventricular synchronous pacing, asynchronous pacing, triggered pacing, cardiac resynchronization pacing, or tachycardia-related therapy. A tissue-piercing electrode is implanted in the basal and/or septal region of the left ventricular myocardium of the patient's heart from the triangle of Koch region of the right atrium through the right atrial endocardium and central fibrous body to facilitate the VfA cardiac therapy.

In one aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The plurality of electrodes also includes a right atrial electrode positionable within the right atrium to at least one of deliver cardiac therapy and sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor electrical activity of the right atrium using the right atrial electrode and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity of the right atrium.

In another aspect, the present disclosure relates to a method that includes monitoring activity of the right atrium of a patient's heart using a right atrial electrode or a right atrial motion detector and delivering atrioventricular synchronous pacing using at least a tissue-piercing electrode implanted in the basal and/or septal region of the left ventricular myocardium of the patient's heart from the triangle of Koch region of the right atrium through the right atrial endocardium and central fibrous body including pacing one or both ventricles using at least the tissue-piercing electrode based on the monitored activity of the right atrium.

In another aspect, the present disclosure relates to an implantable medical device that includes a housing extending from a proximal end region to a distal end region. The device also includes a plurality of electrodes. The plurality of electrodes includes a tissue-piercing electrode leadlessly coupled to the distal end region of the housing and implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode leadlessly coupled to the housing and positionable within the right atrium to deliver cardiac therapy to or sense electrical activity of the right atrium of the patient's heart. The implantable medical device also includes a therapy delivery circuit within the housing operably coupled to the plurality of electrodes to deliver cardiac therapy to the patient's heart and a sensing circuit within the housing operably coupled to the plurality of electrodes to sense electrical activity of the patient's heart. The implantable medical device further includes a controller including processing circuitry within the housing operably coupled to the therapy delivery circuit and the sensing circuit. The controller is configured to monitor electrical activity of the right atrium using the right atrial electrode and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity of the right atrium.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The tissue-piercing electrode also includes a right atrial motion detector positionable within the right atrium to sense mechanical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor mechanical activity of the right atrium using the right atrial motion detector and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored mechanical activity of the right atrium.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to at least one of deliver cardiac therapy to or sense electrical activity of the left ventricle in the basal and/or septal region of the left ventricular myocardium of a patient's heart. The plurality of electrodes also includes a right atrial electrode positionable within the right atrium to at least one of deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor at least one of electrical activity of the right atrium using the right atrial electrode and electrical activity of the left ventricle using the tissue-piercing electrode implanted in the basal and/or septal region of the left ventricular myocardium of the patient's heart from the triangle of Koch region of the right atrium through the right atrial endocardium and central fibrous body. The controller is also configured to deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity.

In another aspect, the present disclosure relates to a method that includes monitoring at least one of electrical activity of the right atrium of a patient's heart using a right atrial electrode and electrical activity of the left ventricle using a tissue-piercing electrode implanted in the basal and/or septal region of the left ventricular myocardium of the patient's heart from the triangle of Koch region of the right atrium through the right atrial endocardium and central fibrous body. The method also includes delivering cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body including pacing one or both ventricles based on the monitored electrical activity.

In another aspect, the present disclosure relates to an implantable medical device that includes a housing extending from a proximal end region to a distal end region. The implantable medical device also includes a plurality of electrodes. The plurality of electrodes includes a tissue-piercing electrode leadlessly coupled to the distal end region of the housing and implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode leadlessly coupled to the housing and positionable within the right atrium to deliver cardiac therapy to or sense electrical activity of the right atrium of the patient's heart. The implantable medical device also includes a therapy delivery circuit within the housing operably coupled to the plurality of electrodes to deliver cardiac therapy to the patient's heart and a sensing circuit within the housing operably coupled to the plurality of electrodes to sense electrical activity of the patient's heart. The implantable medical device further includes a controller including processing circuitry within the housing operably coupled to the therapy delivery circuit and the sensing circuit. The controller is configured to monitor at least one of electrical activity of the right atrium using the right atrial electrode and electrical activity of the left ventricle using the tissue-piercing electrode in the basal and/or septal region of the left ventricular myocardium of the patient's heart from the triangle of Koch region of the right atrium through the right atrial endocardium and central fibrous body. The controller is further configured to deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The plurality of electrodes also includes a right atrial motion detector positionable within the right atrium to sense mechanical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor mechanical activity of the right atrium using the right atrial motion detector and deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored mechanical activity of the right atrium.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to: monitor electrical activity of the right atrium using the right atrial electrode; monitor electrical activity of the left ventricle using the tissue-piercing electrode implanted in the basal and/or septal region of the left ventricular myocardium of the patient's heart from the triangle of Koch region of the right atrium through the right atrial endocardium and central fibrous body to sense electrical activity of the left ventricle in the basal and/or septal region of the left ventricular myocardium; and deliver tachycardia therapy based on the monitored electrical activities of the right atrium and the left ventricle.

In another aspect, the present disclosure relates to a method that includes monitoring electrical activity of the right atrium of a patient's heart using a right atrial electrode; monitoring electrical activity of the left ventricle of the patient's heart using a tissue-piercing electrode implanted in the basal and/or septal region of the left ventricular myocardium of the patient's heart from the triangle of Koch region of the right atrium through the right atrial endocardium and central fibrous body to sense electrical activity of the left ventricle in the basal and/or septal region of the left ventricular myocardium; and deliver tachycardia therapy based on the monitored electrical activities of the right atrium and the left ventricle.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to: monitor electrical activity of the right atrium using the right atrial electrode; monitor electrical activity of the left ventricle using the tissue-piercing electrode implanted to sense electrical activity of the left ventricle in the basal and/or septal region of the left ventricular myocardium of the patient's heart from the triangle of Koch region of the right atrium through the right atrial endocardium and central fibrous body; and determine tachycardia of the patient's heart based on the monitored electrical activities of the right atrium and the left ventricle.

In another aspect, the present disclosure relates to an implantable medical device that includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to deliver at least one of anti-tachycardia pacing therapy using the plurality of electrodes and shock therapy using a separate medical device.

The above summary is not intended to describe each embodiment or every implementation of the present disclosure. A more complete understanding will become apparent and appreciated by referring to the following detailed description and claims taken in conjunction with the accompanying drawings. In other words, these and various other features and advantages will be apparent from a reading of the following detailed description.

DETAILED DESCRIPTION

Figure 1:
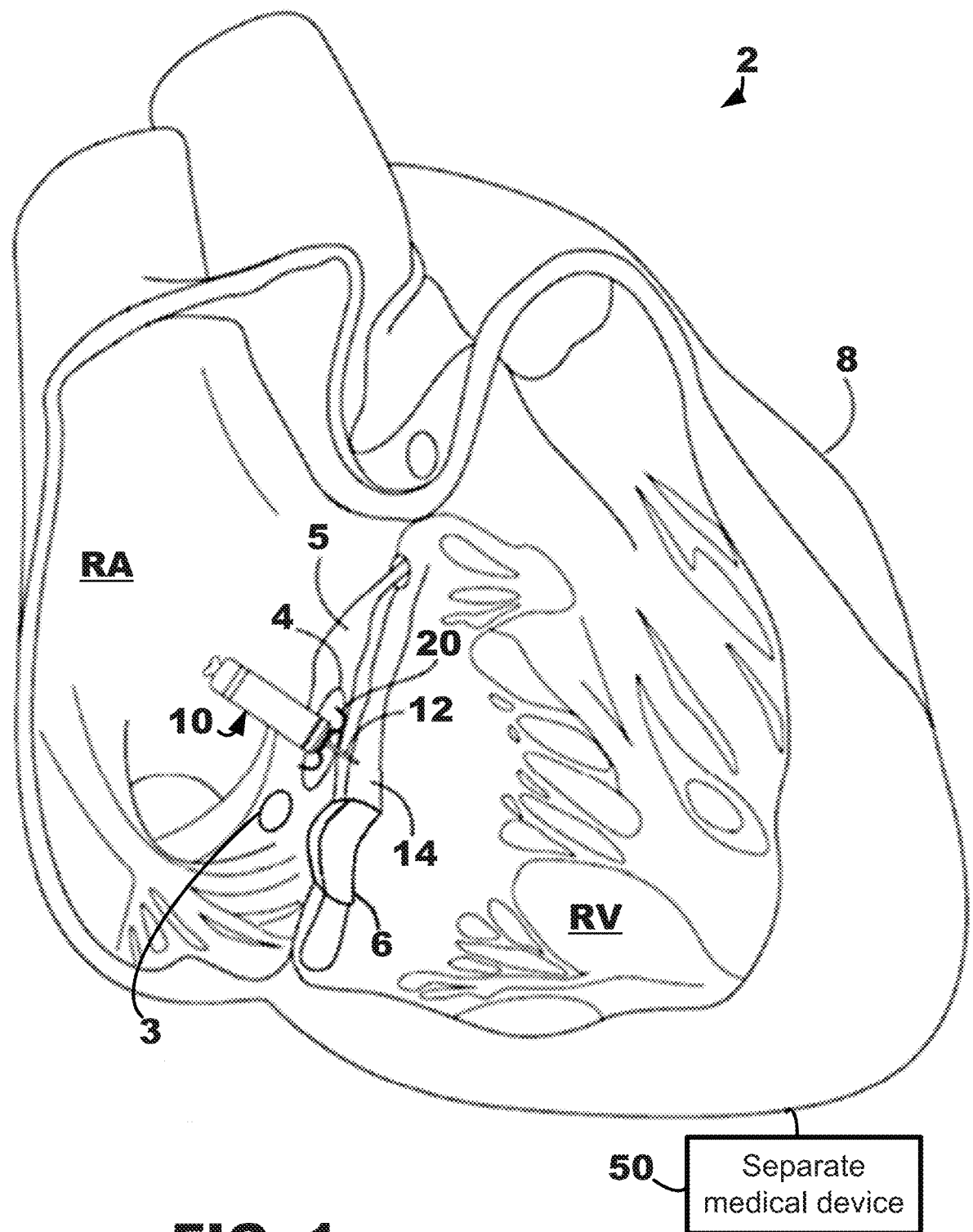
FIG. 1 is a conceptual diagram of an illustrative cardiac therapy system including an intracardiac medical device implanted in a patient's heart shown in a cross-sectional view and a separate medical device positioned outside of the patient's heart.

This disclosure relates to implantable medical devices, systems, and methods for VfA cardiac therapy, including single or multiple chamber pacing (e.g., dual or triple chamber pacing), atrioventricular synchronous pacing, asynchronous pacing, triggered pacing, cardiac resynchronization pacing, or tachycardia-related therapy. Although reference is made herein to implantable medical devices, such as a pacemaker or ICD, the methods and processes may be used with any medical devices, systems, or methods related to a patient's heart. Various other applications will become apparent to one of skill in the art having the benefit of the present disclosure.

It may be beneficial to provide an implantable medical device that is free of transvenous leads (e.g., a leadless device). It may also be beneficial to provide an implantable medical device capable of being used for various cardiac therapies, such as single or multiple chamber pacing (e.g., dual or triple chamber pacing), atrioventricular synchronous pacing, asynchronous pacing, triggered pacing, cardiac resynchronization pacing, or tachycardia-related therapy. Further, it may be beneficial to provide a system capable of communicating with a separate medical device, for example, to provide triggered pacing or to provide shock therapy in certain cases of tachycardia.

The present disclosure provides an implantable medical device including a tissue-piercing electrode and optionally a right atrial electrode and/or a right atrial motion detector. The tissue-piercing electrode may be implanted in the basal and/or septal region of the left ventricular myocardium of the patient's heart from the triangle of Koch region of the right atrium through the right atrial endocardium and central fibrous body. In a leadless implantable medical device, the tissue-piercing electrode may leadlessly extend from a distal end region of a housing of the device, and the right atrial electrode may be leadlessly coupled to the housing (e.g., part of or positioned on the exterior of). The right atrial motion detector may be within the implantable medical device. In a leaded implantable medical device, one or more of the electrodes may be coupled to the housing using an implantable lead. When the device is implanted, the electrodes may be used to sense electrical activity in one or more atria and/or ventricles of a patient's heart. The motion detector may be used to sense mechanical activity in one or more atria and/or ventricles of the patient's heart. In particular, the activity of the right atrium and the left ventricle may be monitored and, optionally, the activity of the right ventricle may be monitored. The electrodes may be used to deliver cardiac therapy, such as single chamber pacing for atrial fibrillation, atrioventricular synchronous pacing for bradycardia, asynchronous pacing, triggered pacing, cardiac resynchronization pacing for ventricular dyssynchrony, anti-tachycardia pacing, or shock therapy. Shock therapy may be initiated by the implantable medical device. A separate medical device, such as an extravascular ICD, which may also be implanted, may be in operative communication with the implantable medical device and may deliver an electrical shock in response to a trigger, such as a signaling pulse (e.g., triggering, signaling, or distinctive electrical pulse) provided by the device.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

Although the present disclosure describes leadless and leaded implantable medical devices, reference is first made to FIG. 1 showing a conceptual diagram of a cardiac therapy system 2 including an intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device against the atrial endocardium in a target implant region 4. The target implant region 4 may lie between the Bundle of His 5 and the coronary sinus 3 and may be adjacent the tricuspid valve 6. The device 10 may be described as a ventricle-from-atrium (VfA) device, which may sense or provide therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. In other words, a leadless device may have a lead that does not extend from outside of the patient's heart to inside of the patient's heart. Some leadless devices may be introduced through a vein, but once implanted, the device is free of, or may not include, any transvenous lead and may be configured to provide cardiac therapy without using any transvenous lead. A leadless VfA device, in particular, does not use a lead to operably connect to an electrode in the ventricle when a housing of the device is positioned in the atrium. A leadless electrode may be coupled to the housing of the medical device without using a lead between the electrode and the housing.

The device 10 may include one or more dart electrodes 12 having a straight shaft extending from the distal end region of device 10, through the atrial myocardium and the central fibrous body, and into the ventricular myocardium 14 or along the ventricular septum, without perforating entirely through the ventricular endocardial or epicardial surfaces. In other words, the dart electrode 12 may not pierce through the ventricular wall into the blood volume. The dart electrode 12 may carry an electrode at the distal end region of the shaft for positioning the electrode within the ventricular myocardium for sensing ventricular signals and delivering ventricular pulses (e.g., to depolarize the left ventricle to initiate a contraction of the left ventricle). In some examples, the electrode at the distal end region of the shaft is a cathode electrode provided for use in a bipolar electrode pair for pacing and sensing. While the implant region 4 is shown in FIG. 1 to enable one or more electrodes of the one or more dart electrodes 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

The cardiac therapy system 2 may also include a separate medical device 50 (depicted diagrammatically in FIG. 1), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead with a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy, e.g., the defibrillation shocks provided by the defibrillation electrode of the defibrillation lead, separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may include a sensing circuit. The sensing circuit may be configured to obtain electrical signals sensed via one or more combinations of electrodes and process the obtained signals. The components of the sensing circuit may be analog components, digital components, or a combination thereof. The sensing circuit may, for example, include one or more sense amplifiers, filters, rectifiers, threshold detectors, analog-to-digital converters (ADCs) or the like. The sensing circuit may convert the sensed signals to digital form and provide the digital signals to the control circuit for processing or analysis. For example, the sensing circuit may amplify signals from sensing electrodes and convert the amplified signals to multi-bit digital signals by an ADC. The sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 2:
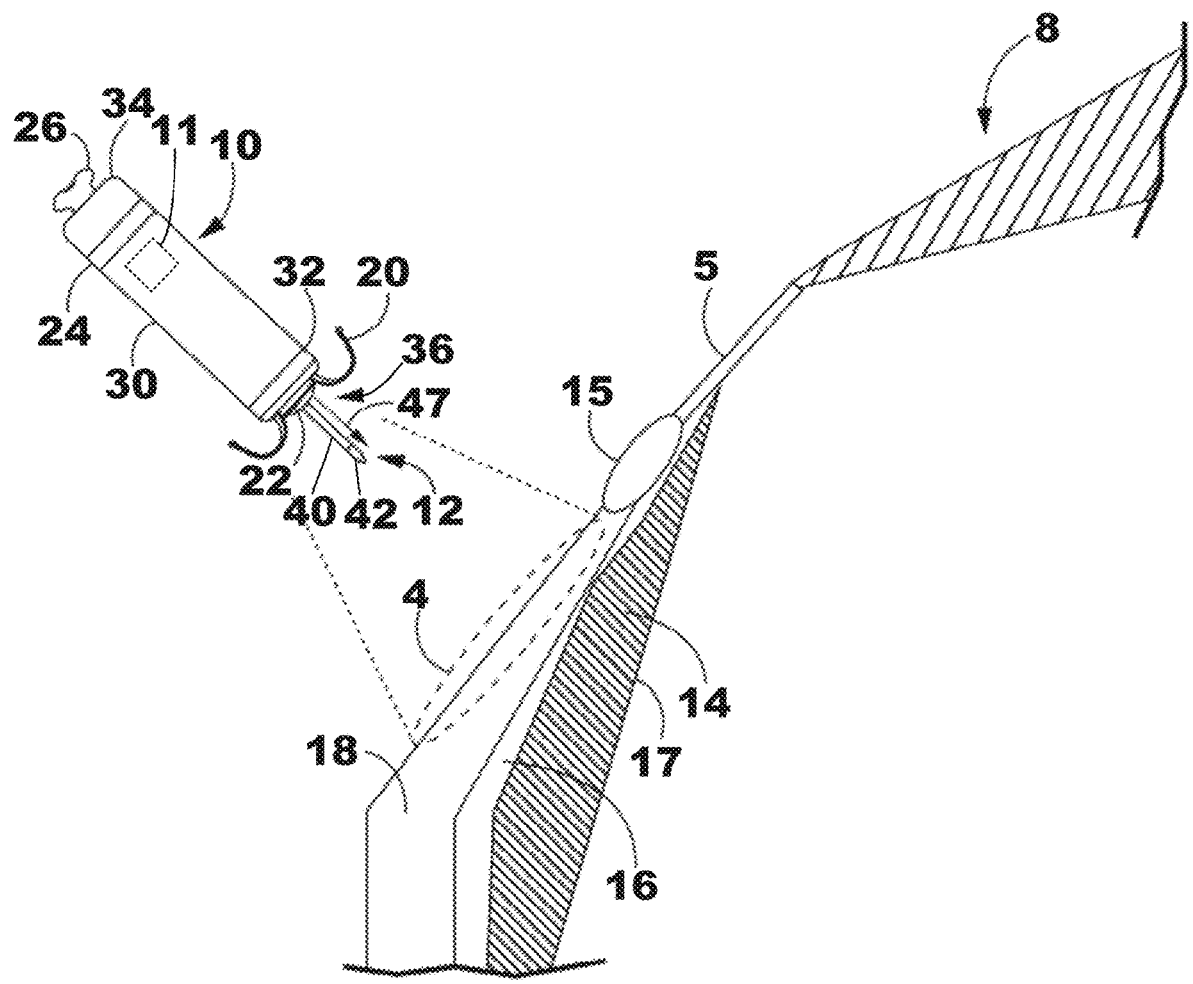
FIG. 2 is an enlarged conceptual diagram of the intracardiac medical device of FIG. 1 and anatomical structures of the patient's heart.

FIG. 2 is an enlarged conceptual diagram of the intracardiac medical device 10 and anatomical structures of the patient's heart 8. The intracardiac device 10 may include a housing 30. The housing 30 may define a hermetically sealed internal cavity in which internal components of the device 10 reside, such as a sensing circuit, therapy delivery circuit, control circuit, memory, telemetry circuit, other optional sensors, and a power source as generally described in conjunction with FIG. 4 below. The housing 30 may be formed from an electrically conductive material including titanium or titanium alloy, stainless steel, MP35N (a non-magnetic nickel-cobalt-chromium-molybdenum alloy), platinum alloy or other bio-compatible metal or metal alloy. In other examples, the housing 30 may be formed from a non-conductive material including ceramic, glass, sapphire, silicone, polyurethane, epoxy, acetyl co-polymer plastics, polyether ether ketone (PEEK), a liquid crystal polymer, or other biocompatible polymer.

The housing 30 may be described as extending between a distal end region 32 and a proximal end region 34 in a generally cylindrical shape to facilitate catheter delivery. In other embodiments, the housing 30 may be prismatic or any other shape so as to perform the functionality and utility described herein. The housing 30 may include a delivery tool interface member 26, e.g., at the proximal end 34, for engaging with a delivery tool during implantation of the device 10.

All or a portion of the housing 30 may function as an electrode during cardiac therapy, for example, in sensing and/or pacing. In the example shown, the housing-based electrode 24 is shown to circumscribe a proximal portion of the housing 30. When the housing 30 is formed from an electrically conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to define the proximal housing-based electrode 24. When the housing 30 is formed from a non-conductive material, such as a ceramic, glass or polymer material, an electrically-conductive coating or layer, such as a titanium, platinum, stainless steel, or alloys thereof, may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32 and is therefore referred to as a "proximal housing-based electrode" 24. In other examples, however, the housing-based electrode 24 may be located at other positions along the housing 30, e.g., relatively more distally than the position shown.

At the distal end region 32, the device 10 may include a distal fixation and electrode assembly 36, which may include one or more fixation members 20, in addition to one or more dart electrodes 12 of equal or unequal length. The dart electrode 12 may include a shaft 40 extending distally away from the housing distal end region 32 and may include one or more electrode elements, such as a tip electrode 42 at or near the free, distal end region of the shaft 40. The tip electrode 42 may have a conical or hemi-spherical distal tip with a relatively narrow tip diameter (e.g., less than about 1 mm) for penetrating into and through tissue layers without using a sharpened tip or needle-like tip having sharpened or beveled edges.

The shaft 40 of the dart electrode 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by the height 47 of the shaft 40. The dart electrode 12 may be configured to pierce through one or more tissue layers to position the tip electrode 42 within a desired tissue layer, e.g., the ventricular myocardium. As such, the height 47 of the shaft 40 may correspond to the expected pacing site depth, and the shaft may have a relatively high compressive strength along its longitudinal axis to resist bending in a lateral or radial direction when pressed against the implant region 4. If a second dart electrode 12 is employed, its length may be unequal to the expected pacing site depth and may be configured to act as an indifferent electrode for delivering of pacing energy to the tissue. A longitudinal axial force may be applied against the tip electrode 42, e.g., by applying longitudinal pushing force to the proximal end 34 of the housing 30, to advance the dart electrode 12 into the tissue within target implant region. The shaft 40 may be longitudinally non-compressive. The shaft 40 may be elastically deformable in lateral or radial directions when subjected to lateral or radial forces to allow temporary flexing, e.g., with tissue motion, but may return to its normally straight position when lateral forces diminish. When the shaft 40 is not exposed to any external force, or to only a force along its longitudinal central axis, the shaft 40 may retain a straight, linear position as shown.

The one or more fixation members 20 may be described as one or more "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode 42 may define the height 47 of the shaft 40 for penetrating through the atrial endocardium 18 in the target implant region 4, through the central fibrous body 16, and into the ventricular myocardium 14 without perforating through the ventricular endocardial surface 17. When the height 47 of the dart electrode 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode 12 may have a total combined height 47 of tip electrode 42 and shaft 40 from about 3 mm to about 8 mm in various examples. The diameter of the shaft 40 may be less than about 2 mm, and may be about 1 mm or less, or even about 0.6 mm or less.

The device 10 may include a motion detector 11 within the housing 30. The motion detector 11 may be used to monitor mechanical activity, such as atrial mechanical activity (e.g., an atrial contraction) and/or ventricular mechanical activity (e.g., a ventricular contraction). In some embodiments, the motion detector 11 may be used to detect right atrial mechanical activity. A non-limiting example of a motion detector 11 includes an accelerometer. In some embodiments, the mechanical activity detected by the motion detector 11 may be used to supplement or replace electrical activity detected by one or more of the electrodes of the device 10. For example, the motion detector 11 may be used in addition to, or as an alternative to, the proximal housing-based electrode 24.

The motion detector 11 may also be used for rate response detection or to provide a rate-responsive 1 MB. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

Figure 3:
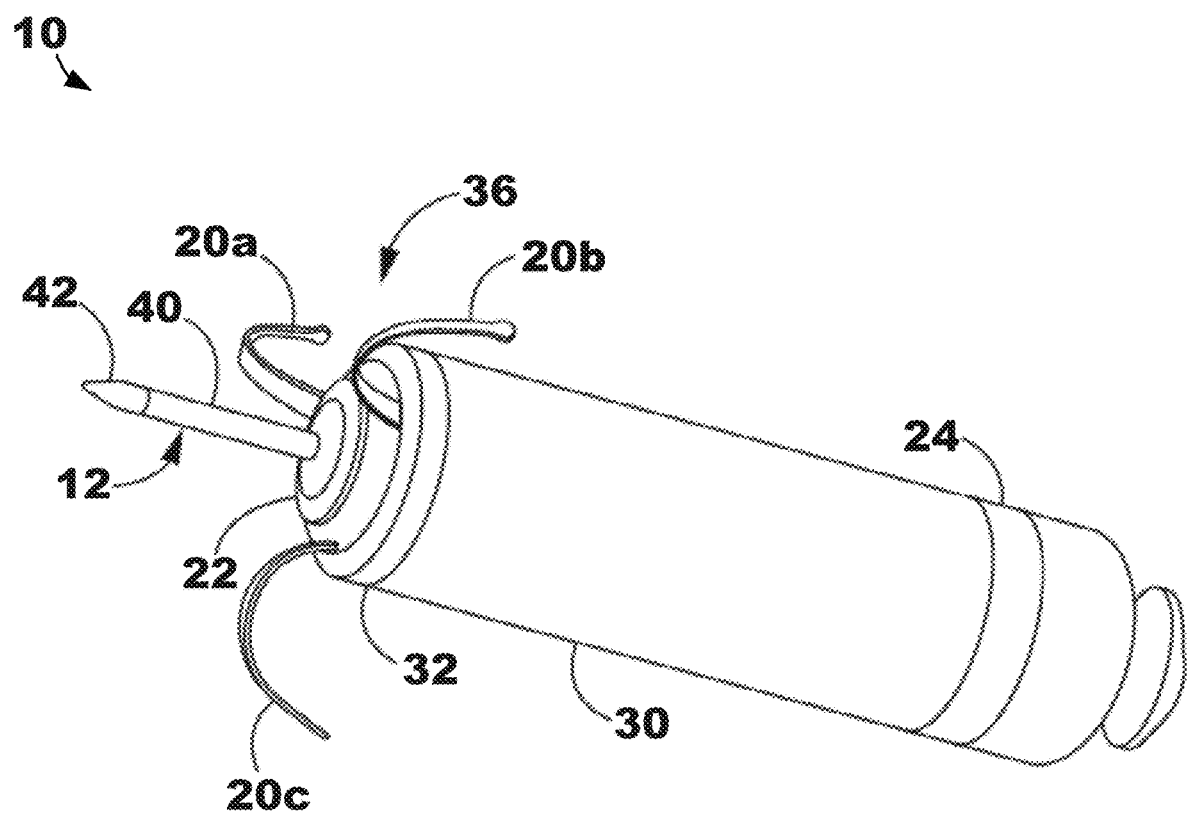
FIG. 3 is a perspective view of the intracardiac medical device of FIGS. 1-2 having a distal fixation and electrode assembly that includes a distal housing-based electrode implemented as a ring electrode.

FIG. 3 is a three-dimensional perspective view of the device 10 capable of cardiac therapy. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines 20a, 20b and 20c of the fixation members 20, engage with the atrial tissue. The tines 20a, 20b and 20c, which may be elastically deformable, may be extended distally during delivery of device 10 to the implant site. For example, the tines 20a, 20b, and 20c may pierce the atrial endocardial surface as the device 10 is advanced out of the delivery tool and flex back into their normally curved position (as shown) when no longer constrained within the delivery tool. As the tines 20a, 20b and 20c curve back into their normal position, the fixation member 20 may pull the distal fixation member and electrode assembly 36 toward the atrial endocardial surface. As the distal fixation member and electrode assembly 36 is pulled toward the atrial endocardium, the tip electrode 42 may be advanced through the atrial myocardium and the central fibrous body and into the ventricular myocardium. The distal housing-based electrode 22 may then be positioned against the atrial endocardial surface.

The distal housing-based electrode 22 may include a ring formed of an electrically conductive material, such as titanium, platinum, iridium, or alloys thereof. The distal housing-based electrode 22 may be a single, continuous ring electrode. In other examples, portions of the ring may be coated with an electrically insulating coating, e.g., parylene, polyurethane, silicone, epoxy, or other insulating coating, to reduce the electrically conductive surface area of the ring electrode. For instance, one or more sectors of the ring may be coated to separate two or more electrically conductive exposed surface areas of the distal housing-based electrode 22. Reducing the electrically conductive surface area of the distal housing-based electrode 22, e.g., by covering portions of the electrically conductive ring with an insulating coating, may increase the electrical impedance of the distal housing-based 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 4:
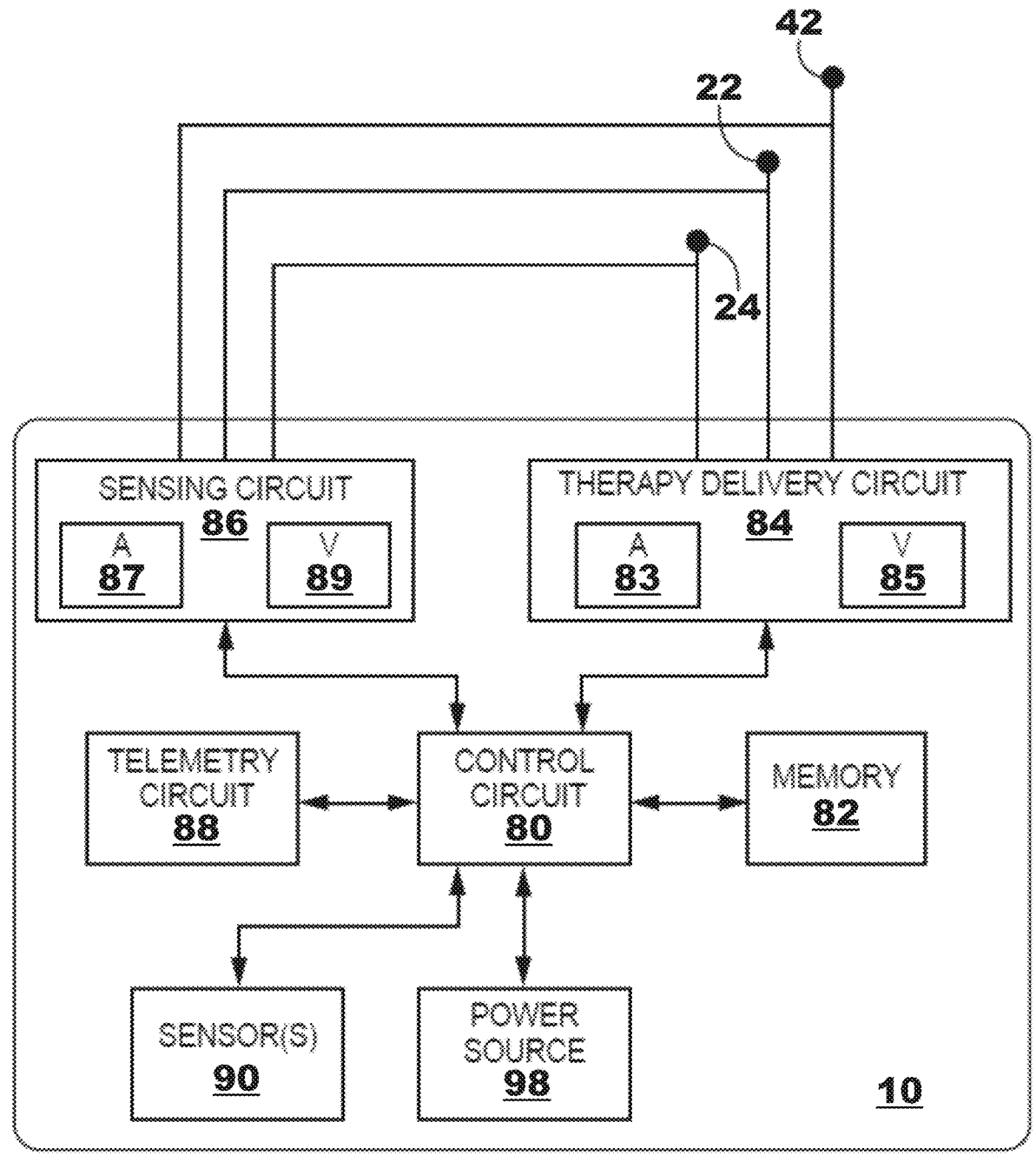
FIG. 4 is a block diagram of illustrative circuitry that may be enclosed within a housing of the intracardiac medical device of FIGS. 1-3, for example, to provide the functionality and therapy described herein.

FIG. 4 is a block diagram of circuitry that may be enclosed within the housing 30 (FIG. 3) to provide the functions of cardiac therapy using the device 10 according to one example. The separate medical device 50 (FIG. 1) may include some or all the same components, which may be configured in a similar manner. The electronic circuitry enclosed within housing 30 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate.

The power source 98 may provide power to the circuitry of the device 10 including each of the components 80, 82, 84, 86, 88, and 90 as needed. The power source 98 may include one or more energy storage devices, such as one or more rechargeable or non-rechargeable batteries. The connections between the power source 98 and each of the components 80, 82, 84, 86, 88, and 90 are to be understood from the general block diagram illustrated but are not shown for the sake of clarity. For example, the power source 98 may be coupled to one or more charging circuits included in the therapy delivery circuit 84 for providing the power needed to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

Any suitable technique may be used to recharge a rechargeable power source 98. In some embodiments, the device 10 may include an antenna, inductive coils, or other inductive coupling structures configured to couple to another device, such as an external charger or programmer, to receive power in situ. Various examples of charging a leadless implantable medical device are described in U.S. Patent Pub. No. 2018/0212451 (Schmidt et al.), filed Jan. 26, 2017, entitled "Recharge of Implanted Medical Devices," which is incorporated herein by reference in its entirety. The device 10 may also be configured to use various techniques to extend the life of the power source 98, such as a low-power mode.

Various examples of power sources and techniques related to power sources may be used, such as those found in, for example, U.S. Pat. No. 8,383,269 (Scott et al.), granted Feb. 26, 2013, U.S. Pat. No. 8,105,714 (Schmidt et al.), granted Jan. 31, 2012, and U.S. Pat. No. 7,635,541 (Scott et al.), granted Dec. 22, 2009, each of which is incorporated herein by reference in its entirety.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device. Providing software, hardware, and/or firmware to accomplish the described functionality in the context of any modern cardiac medical device system, given the disclosure herein, is within the abilities of one of skill in the art.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to perform a single, dual, or triple chamber pacing (e.g., single or multiple chamber pacing) function or other sensing and therapy delivery functions attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., PP intervals between consecutive P-wave sensed event signals received from the atrial sensing channel 87, RR intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83 and 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83 or 85. The tip electrode 42 and the proximal housing-based electrode 24 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual or triple chamber pacing).

Charging of a holding capacitor of the atrial or ventricular pacing circuit 83 or 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

The device 10 may include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by the control circuit 80 for use in determining a sensor-indicated pacing rate.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

Figure 5:
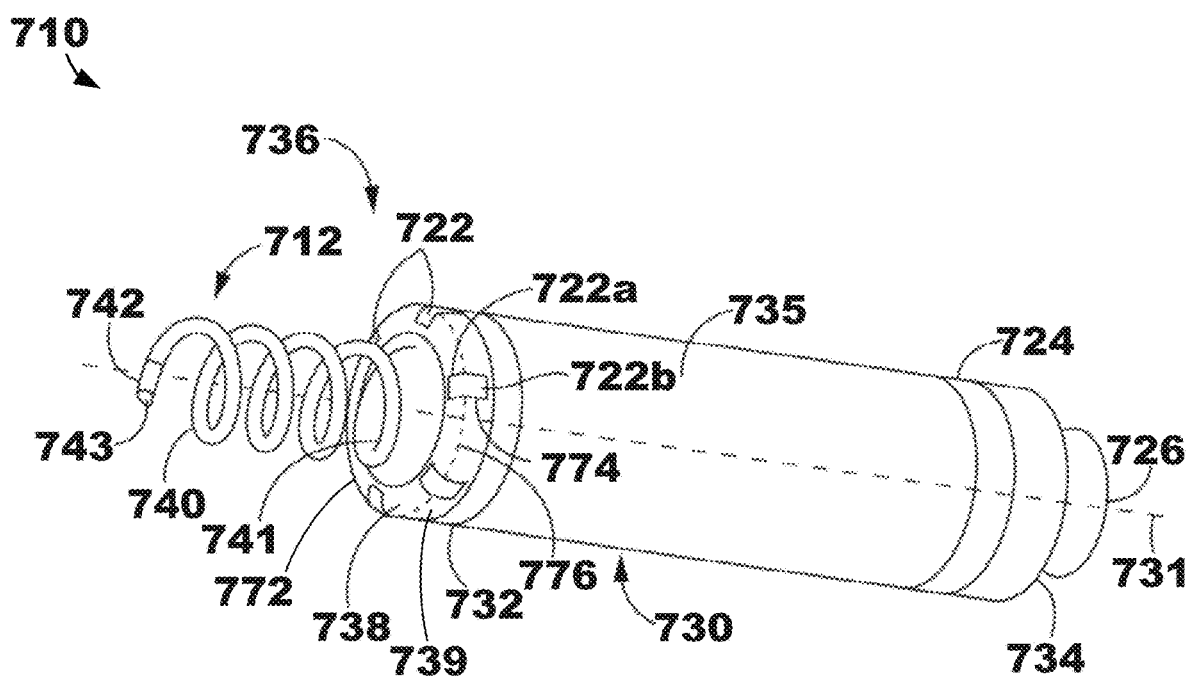
FIG. 5 is a perspective view of another illustrative intracardiac medical device for use with, e.g., the illustrative system and device of FIGS. 1-4.

FIG. 5 is a three-dimensional perspective view of another leadless intracardiac medical device 710 that may be configured for single or multiple chamber cardiac therapy (e.g., dual or triple chamber cardiac therapy) according to another example. The device 710 may include a housing 730 having an outer sidewall 735, shown as a cylindrical outer sidewall, extending from a housing distal end region 732 to a housing proximal end region 734. The housing 730 may enclose electronic circuitry configured to perform single or multiple chamber cardiac therapy, including atrial and ventricular cardiac electrical signal sensing and pacing the atrial and ventricular chambers. Delivery tool interface member 726 is shown on the housing proximal end region 734.

A distal fixation and electrode assembly 736 may be coupled to the housing distal end region 732. The distal fixation and electrode assembly 736 may include an electrically insulative distal member 772 coupled to the housing distal end region 732. The tissue piercing electrode 712 extends away from the housing distal end region 732, and multiple non-tissue piercing electrodes 722 may be coupled directly to the insulative distal member 772. The tissue piercing electrode 712 extends in a longitudinal direction away from the housing distal end region 732 and may be coaxial with the longitudinal center axis 731 of the housing 730.

The tissue piercing distal electrode 712 may include an electrically insulated shaft 740 and a tip electrode 742. In some examples, the tissue piercing distal electrode 712 is an active fixation member including a helical shaft 740 and a distal cathode tip electrode 742. The helical shaft 740 may extend from a shaft distal end region 743 to a shaft proximal end region 741, which may be directly coupled to the insulative distal member 772. The helical shaft 740 may be coated with an electrically insulating material, e.g., parylene or other examples listed herein, to avoid sensing or stimulation of cardiac tissue along the shaft length. The tip electrode 742 is at the shaft distal end region 743 and may serve as a cathode electrode for delivering ventricular pacing pulses and sensing ventricular electrical signals using the proximal housing-based electrode 724 as a return anode when the tip electrode 742 is advanced into ventricular tissue. The proximal housing-based electrode 724 may be a ring electrode circumscribing the housing 730 and may be defined by an uninsulated portion of the longitudinal sidewall 735. Other portions of the housing 730 not serving as an electrode may be coated with an electrically insulating material as described above in conjunction with FIG. 2.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more of a dart-type electrode (e.g., electrode 12 of FIGS. 1-2), a helical-type electrode (e.g., electrode 712) Non-limiting examples of multiple tissue-piercing electrodes include two dart electrodes, a helix electrode with a dart electrode extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically active and electrically separate elements, which may enable bipolar or multi-polar pacing from one or more tissue-piercing electrodes.

Multiple non-tissue piercing electrodes 722 may be provided along a periphery of the insulative distal member 772, peripheral to the tissue piercing electrode 712. The insulative distal member 772 may define a distal-facing surface 738 of the device 710 and a circumferential surface 739 that circumscribes the device 710 adjacent to the housing longitudinal sidewall 735. Non-tissue piercing electrodes 722 may be formed of an electrically conductive material, such as titanium, platinum, iridium, or alloys thereof. In the illustrated embodiment, six non-tissue piercing electrodes 722 are spaced apart radially at equal distances along the outer periphery of insulative distal member 772, however, two or more non-tissue piercing electrodes 722 may be provided.

Non-tissue piercing electrodes 722 may be discrete components each retained within a respective recess 774 in the insulative member 772 sized and shaped to mate with the non-tissue piercing electrode 722. In other examples, the non-tissue piercing electrodes 722 may each be an uninsulated, exposed portion of a unitary member mounted within or on the insulative distal member 772. Intervening portions of the unitary member not functioning as an electrode may be insulated by the insulative distal member 772 or, if exposed to the surrounding environment, may be coated with an electrically insulating coating, e.g., parylene, polyurethane, silicone, epoxy, or other insulating coating.

When the tissue piercing electrode 712 is advanced into cardiac tissue, at least one non-tissue piercing electrode 722 may be positioned against, in intimate contact with, or in operative proximity to, a cardiac tissue surface for delivering pulses and/or sensing cardiac electrical signals produced by the patient's heart. For example, non-tissue piercing electrodes 722 may be positioned in contact with right atrial endocardial tissue for pacing and sensing in the atrium when the tissue piercing electrode 712 is advanced into the atrial tissue and through the central fibrous body until the distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and the sensing circuit 86 (see FIG. 4) enclosed by the housing 730 to function collectively as a cathode electrode for delivering atrial pacing pulses and for sensing atrial electrical signals, e.g., P-waves, in combination with the proximal housing-based electrode 724 as a return anode. Switching circuitry included in the sensing circuit 86 may be activated under the control of the control circuit 80 to couple one or more of the non-tissue piercing electrodes to the atrial sensing channel 87. Distal, non-tissue piercing electrodes 722 may be electrically isolated from each other so that each individual one of the electrodes 722 may be individually selected by switching circuitry included in the therapy delivery circuit 84 to serve alone or in a combination of two or more of the electrodes 722 as an atrial cathode electrode. Switching circuitry included in the therapy delivery circuit 84 may be activated under the control of the control circuit 80 to couple one or more of the non-tissue piercing electrodes 722 to the atrial pacing circuit 83. Two or more of the non-tissue piercing electrodes 722 may be selected at a time to operate as a multi-point atrial cathode electrode.

Certain non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from the power source 98.

In some instances, the distal-facing surface 738 may uniformly contact the atrial endocardial surface when the tissue piercing electrode 712 anchors the housing 730 at the implant site. In that case, all the electrodes 722 may be selected together to form the atrial cathode. Alternatively, every other one of the electrodes 722 may be selected together to form a multi-point atrial cathode having a higher electrical impedance that is still uniformly distributed along the distal-facing surface 738. Alternatively, a subset of one or more electrodes 722 along one side of the insulative distal member 772 may be selected to provide pacing at a desired site that achieves the lowest pacing capture threshold due to the relative location of the electrodes 722 to the atrial tissue being paced.

In other instances, the distal-facing surface 738 may be oriented at an angle relative to the adjacent endocardial surface depending on the positioning and orientation at which the tissue piercing electrode 712 enters the cardiac tissue. In this situation, one or more of the non-tissue piercing electrodes 722 may be positioned in closer contact with the adjacent endocardial tissue than other non-tissue piercing electrodes 722, which may be angled away from the endocardial surface. By providing multiple non-tissue piercing electrodes along the periphery of the insulative distal member 772, the angle of the tissue piercing electrode 712 and the housing distal end region 732 relative to the cardiac surface, e.g., the right atrial endocardial surface, may not be required to be substantially parallel. Anatomical and positional differences may cause the distal-facing surface 738 to be angled or oblique to the endocardial surface, however, multiple non-tissue piercing electrodes 722 distributed along the periphery of the insulative distal member 772 increase the likelihood of good contact between one or more electrodes 722 and the adjacent cardiac tissue to promote acceptable pacing thresholds and reliable cardiac event sensing using at least a subset of multiple electrodes 722. Contact or fixation circumferentially along the entire periphery of the insulative distal member 772 may not be required.

The non-tissue piercing electrodes 722 are shown to each include a first portion 722a extending along the distal-facing surface 738 and a second portion 722b extending along the circumferential surface 739. The first portion 722a and the second portion 722b may be continuous exposed surfaces such that the active electrode surface wraps around a peripheral edge 776 of the insulative distal member 772 that joins the distal facing surface 738 and the circumferential surface 739. The non-tissue piercing electrodes 722 may include one or more of the electrodes 772 along the distal-facing surface 738, one or more electrodes along the circumferential surface 739, one or more electrodes each extending along both of the distal-facing surface 738 and the circumferential surface 739, or any combination thereof. The exposed surface of each of the non-tissue piercing electrodes 722 may be flush with respective distal-facing surfaces 738 and/or circumferential surfaces. In other examples, each of the non-tissue piercing electrodes 722 may have a raised surface that protrudes from the insulative distal member 772. Any raised surface of the electrodes 722, however, may define a smooth or rounded, non-tissue piercing surface.

The distal fixation and electrode assembly 736 may seal the distal end region of the housing 730 and may provide a foundation on which the electrodes 722 are mounted. The electrodes 722 may be referred to as housing-based electrodes. The electrodes 722 may not be not carried by a shaft or other extension that extends the active electrode portion away from the housing 730, like the distal tip electrode 742 residing at the distal tip of the helical shaft 740 extending away from the housing 730. Other examples of non-tissue piercing electrodes presented herein that are coupled to a distal-facing surface and/or a circumferential surface of an insulative distal member include the distal housing-based ring electrode 22 (FIG. 3), the distal housing-based ring electrode extending circumferentially around the assembly 36 (FIG. 3), button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal ring electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue piercing electrode provided along the distal fixation and electrode assembly 736. The atrial chamber walls are relatively thin compared to ventricular chamber walls. A tissue piercing atrial cathode electrode may extend too deep within the atrial tissue leading to inadvertent sustained or intermittent capture of ventricular tissue. A tissue piercing atrial cathode electrode may lead to interference with sensing atrial signals due to ventricular signals having a larger signal strength in the cardiac electrical signal received via tissue-piercing atrial cathode electrodes that are in closer physical proximity to the ventricular tissue. The tissue piercing electrode 712 may be securely anchored into ventricular tissue for stabilizing the implant position of the device 710 and providing reasonable certainty that the tip electrode 742 is sensing and pacing in ventricular tissue while the non-tissue piercing electrodes 722 are reliably pacing and sensing in the atrium. When the device 710 is implanted in the target implant region 4, e.g., as shown in FIG. 1 the ventricular septum, the tip electrode 742 may reach left ventricular tissue for pacing of the left ventricle while the non-tissue piercing electrodes 722 provide pacing and sensing in the right atrium. The tissue piercing electrode 712 may be in the range of about 4 to about 8 mm in length from the distal-facing surface 738 to reach left ventricular tissue. In some instances, the device 710 may achieve four-chamber pacing by delivering atrial pacing pulses from the atrial pacing circuit 83 via the non-tissue piercing electrodes 722 in the target implant region 4 to achieve bi-atrial (right and left atrial) capture and by delivering ventricular pacing pulses from the ventricular pacing circuit 85 via the tip electrode 742 advanced into ventricular tissue from the target implant region 4 to achieve biventricular (right and left ventricular) capture.

FIGS. 6-14 relate to various methods that may be used to position a tissue-piercing electrode of any of the devices described herein, for example, those shown in FIGS. 1-5 and 16-18. In particular, each of the methods may be used when the tissue-piercing electrode is positioned, or implanted, in the basal and/or septal region of the left ventricular myocardium of the patient's heart from the triangle of Koch region of the right atrium through the right atrial endocardium and central fibrous body.

Figure 6:
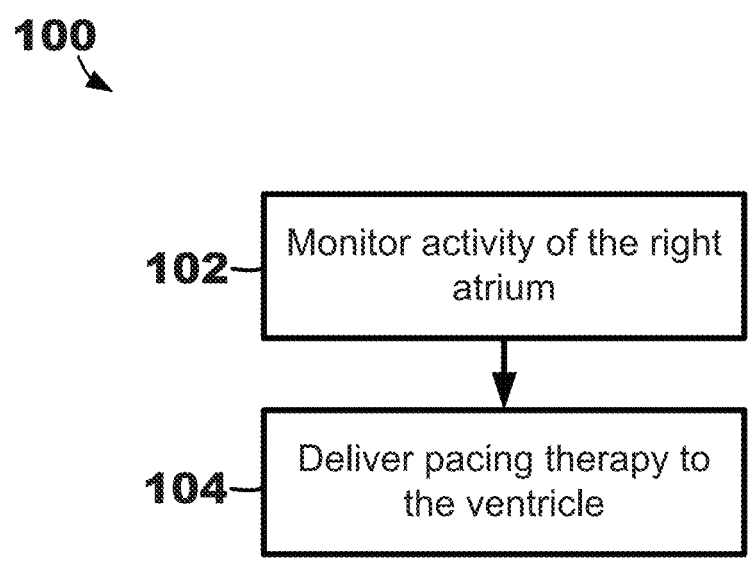
FIG. 6 is a flowchart of an illustrative cardiac therapy method for use with, e.g., the illustrative system and devices of FIGS. 1-5.

FIG. 6 is a flowchart of a cardiac therapy method 100 for use with, e.g., the system 2 of FIG. 1. For example, the method 100 may be used with the intracardiac medical device 10 (FIG. 1-2) or 710 (FIG. 5). The method 100 may be used to describe single chamber or multiple chamber pacing (e.g., dual or triple chamber pacing), atrioventricular synchronous pacing, triggered pacing, cardiac resynchronization pacing, or tachycardia-related therapy.

The method 100 may include process 102, in which activity of the right atrium is monitored. The medical device may use one or more of a plurality of electrodes to monitor the electrical activity of the patient's heart. For example, when implanted, a right atrial electrode (e.g., proximal housing-based electrode 24 or distal housing-based electrode 22 of FIG. 2) may be positioned to sense electrical activity of the right atrium. In some embodiments, the right atrial electrode may be positioned in the volume of the right atrium or against the right atrial endocardial surface of the patient's heart. In some embodiments, the right atrial electrode may be used to deliver cardiac therapy to the right atrium of the patient's heart. The right atrial electrode may be leadlessly coupled to a housing of the medical device. For example, the right atrial electrode may be positioned at the distal end region of the housing or at a location proximal to the distal end region (e.g., the proximal end region of the housing).

In addition, or as an alternative, to using the right atrial electrode, the medical device may use a motion detector to monitor the mechanical activity of the patient's heart. For example, when implanted, a right atrial motion detector may be positioned to sense mechanical activity of the right atrium. In some embodiments, the right atrial motion detector may be positioned within the implantable medical device 10. In some embodiments, the right atrial motion detector may be wirelessly coupled, or coupled using a lead, to the implantable medical device 10. The motion detector may be coupled to the same or a different sensing circuit as the electrodes.

The method 100 may further include process 104, in which pacing therapy is delivered to the ventricle. For example, in process 104, pacing therapy may be delivered to the left ventricle, right ventricle, ventricular septum (e.g., higher posterior basal septum region), or other parts of the ventricular myocardium, in response to the monitored activity of the right atrium in process 102. The monitored activity may include electrical activity, mechanical activity, or both electrical and mechanical activity (e.g., using a right atrial electrode and/or a right atrial motion detector). The medical device may use one or more of the plurality of electrodes to deliver cardiac therapy to the patient's heart. For example, when implanted, a tissue-piercing electrode (e.g., tip electrode 42) may be positioned in the ventricular septum to deliver cardiac therapy to the left ventricle of the patient's heart. The tissue-piercing electrode may be leadlessly coupled to the housing. In some embodiments, the tissue-piercing electrode may be used to sense electrical activity of the left ventricle. The tissue-piercing electrode may extend from a distal end region of the housing.

As mentioned above, the method 100 may be used with cardiac resynchronization pacing (e.g., cardiac resynchronization therapy). In some embodiments using cardiac resynchronization pacing, a pace may be delivered to one or both ventricles in response to a sensed atrial or ventricular event. Examples of cardiac resynchronization pacing include biventricular pacing and monoventricular pacing. Monoventricular pacing may include left ventricular pacing, right ventricular pacing, or fusion pacing. Various methods of performing cardiac resynchronization pacing are described in U.S. Patent Application Pub. No. 2017/0340885 (Sambelashvili), filed 31 Jul. 2017, entitled "Systems and methods for leadless cardiac resynchronization therapy," and U.S. Pat. No. 9,789,319 (Sambelashvili), issued 17 Oct. 2017, entitled "Systems and methods for leadless cardiac resynchronization therapy," each of which is incorporated herein by reference in its entirety.

One type of cardiac resynchronization pacing is biventricular pacing. Biventricular pacing may include pacing the right ventricle (RV) with a RV electrode and a left ventricle (LV) with a LV electrode (e.g., the tissue-piercing electrode), which are typically different electrodes. In one or more embodiments, the implantable medical device can be configured to automatically switch between biventricular pacing and fusion pacing. In general, the primary goal may be to ensure the ventricles are synchronized with each other. Monoventricular pacing, or specifically fusion pacing, may be used instead of biventricular pacing to achieve synchrony. Skilled artisans appreciate that a patient's heart may be treated using adaptive CRT in which biventricular pacing may be delivered during one period of time (e.g., 1 hour, day, week etc.) and at another time, fusion pacing may be delivered to return the ventricles to synchrony. Typically, fusion pacing involves pacing the LV. However, there may be conditions for which the RV may be solely paced.

One type of adaptive CRT is adaptive LV pacing. Adaptive LV pacing may be described as leveraging intrinsic RV conduction by pre-pacing the LV to synchronize with intrinsic RV activation. The timing of the LV pace may be automatically adjusted based on the atrial to intrinsic QRS interval measurement (AV interval). One or more embodiments can set the LV pace to occur at about 70% of the intrinsic AV interval, but at least 40 ms prior to the intrinsic QRS.

One or more other embodiments can configure LV pacing in response to, or based on, a moderately lengthened QRS. For example, if the QRS width exceeds 120 ms, but does not exceed 160 ms, then LV pacing with fusion is selected. Otherwise, if the QRS width is greater than 160 ms, then biventricular (BiV) pacing is selected. Implementing a moderately lengthened QRS threshold may benefit heart failure patients. Efficacies of LV-only pacing or biventricular pacing may be predicted by the moderately lengthened QRS duration. An illustrative moderately lengthened QRS may correspond to a QRS width in the range of 130 ms-150 ms.

Adaptive CRT may use intrinsic AV conduction to determine whether to use biventricular or fusion pacing. In one or more embodiments, the intrinsic AV conduction may be automatically evaluated. In one or more embodiments, the IMD (e.g., an ICD), leadless pacing device (LPD) (e.g., an intracardiac medical device), and/or subcutaneous implantable device (SD) may automatically evaluate intrinsic ventricular conduction based upon QRS duration from the far-field electromyograph (EGM), or right ventricular sense to left ventricular sense (RVs-LVs) interval from the IMD sensing markers is automatically evaluated by the IMD or SD. For further detail, U.S. Pat. No. 4,374,382 issued to Markowitz et al. describes IMD sensing markers, which is incorporated herein by reference in its entirety. Based on the results, fusion pacing (i.e., LV only pacing or RV only pacing) or biventricular pacing may be selected. For example, RVs-LVs interval not exceeding 150 ms could correspond to LV only pacing, whereas >150 ms could switch the algorithm to biventricular pacing. In one or more other embodiments, RVs-LVs interval not exceeding 80 ms corresponds to fusion pacing while greater than 80 ms switches to biventricular pacing. Typically, RVs-LVs are shorter than the corresponding QRS width. Therefore, it takes about 40 ms to sense the onset of QRS in the RV and the final portion of the QRS in the LV is also sensed prior to the QRS end.

Various devices may be used to carry out the functionality of adaptive CRT. In one or more other embodiments, the IMD may track the moderately lengthened QRS over time and then relies on trend data to switch between biventricular pacing and fusion pacing. For example, assume that the moderately lengthened QRS is 120 ms, 125 ms, 130 ms, 135 m, 140 ms, and 145 ms, respectively for 6 consecutive weeks. The increasing trend could trigger the switch to biventricular pacing before the threshold is met for switching to biventricular pacing.

In another embodiment, the SD could send a control signal to the LPD to initiate CRT. The LPD could sense a cardiac signal (i.e., a second electrical signal) from the heart of the patient. Based on the cardiac signal, the LPD could determine whether to deliver CRT to the heart from the LPD. For example, the LPD, based on the second electrical signal, could determine that CRT is not necessary. The LPD could consider whether sensed data meets a pre-specified threshold. For instance, if the QRS width does not exceed 120 ms, the LPD may withhold the delivery of CRT therapy (e.g., the LPD could then signal the SD that CRT should not be delivered based upon the cardiac signal). The SD can be configured to perform a more detailed analysis in which at least one or more parameters (such as at least two parameters) are evaluated. The SD could then send another command signal that confirms, denies, or overrides the LPD.

In another embodiment, the LPD could sense a cardiac signal that indicates a switch between fusion pacing to biventricular pacing should occur and would signal the SD. The SD could be configured to send an override signal to the LPD unless certain conditions are met.

In yet another embodiment, the LPD could determine that biventricular pacing is may be used instead of fusion pacing in contravention to the SD communication. In one embodiment, the LPD would deliver biventricular pacing. In one or more other embodiments, the LPD could determine that fusion pacing may be used instead of biventricular pacing in contravention to the SD communication. In this scenario, the LPD could deliver fusion pacing.

In another embodiment, the SD transmits a control signal to the LPD to initiate CRT. The LPD senses a cardiac signal (i.e., a second electrical signal) from the heart of the patient. Based on the cardiac signal, the LPD could determine whether to deliver CRT or the type of CRT to deliver to the heart from the LPD. In one or more embodiments, the LPD, based on the second electrical signal, could initially determine that CRT should not be used. The initial determination by the LPD could use tests such as a threshold of one or more parameters. In one or more embodiments, the SD could perform a more detailed analysis as to whether CRT should be delivered. Using the sensed data from the LPD and/or SD, the SD could generate another signal to the LPD that either confirms, denies or overrides the LPDs initial determination.

In another embodiment, the LPD could sense a cardiac signal that indicates a switch should occur between fusion pacing to biventricular pacing. Determining whether to switch between fusion pacing and biventricular pacing could be determined based upon one or more parameters (e.g., moderately lengthened QRS, etc.). The LPD could be configured to either automatically switch between fusion pacing and biventricular pacing or to wait until the SD confirms or denies switching between the CRT pacing mode (i.e., fusion pacing and biventricular pacing). The SD could be configured to send a confirmatory signal or a signal denying the LPD switching the pacing mode.

In yet another embodiment, the LPD could determine that biventricular pacing may be used instead of fusion pacing in contravention to the SD communication. In one embodiment, the LPD would deliver biventricular pacing. In one or more other embodiments, the LPD could determine that fusion pacing is required over biventricular pacing in contravention to the SD communication. In this scenario, the LPD could deliver fusion pacing.

In one or more other embodiments, a device having SD-like functionality is implanted into a patient's heart. For example, the SD could function as a conventional ICD or have the SD functionality described herein. Electrical signals are then sensed which includes moderately lengthened QRS duration data from the patient's heart. A determination is made as to whether cardiac resynchronization pacing therapy (CRT pacing) is appropriate based upon the moderately lengthened QRS duration in the sensed electrical signals. The CRT pacing pulses are delivered to the heart using electrodes. In one or more embodiments, the SD can switch between fusion pacing and biventricular pacing based upon data (e.g., moderately lengthened QRS, etc.) sensed from the heart.

In addition, there are even further embodiments that may be implemented with the methods described herein. One or more LPDs carrying one or more electrodes may be implanted within various chambers of the heart of the patient or otherwise in close proximity of the cardiac muscle. At these locations, an LPD may sense ECG signals with high signal-to-noise ratios to detect arrhythmias. In addition, an LPD may provide cardiac pacing at the location of the implanted LPD. In some examples, one or both of SD and LPD may share detected signals or physiological information (e.g., R-R intervals, electrogram morphology measurements, and/or electrocardiograms or electrograms) such that the device receiving such information can determine a condition of patient (e.g., determine whether or not patient is experiencing an arrhythmia and or lack of synchrony between ventricles). Communication between an LPD and a subcutaneous ICD (SICD) is described in U.S. patent application Ser. No. 13/756,085, filed on Jan. 31, 2013, which is incorporated herein by reference in its entirety.

In some examples, communication between the SICD and an LPD may be used to initiate therapy and/or confirm that therapy should be delivered. The SICD may also transmit a communication message to the LPD instructing the LPD to change one or more parameters that define the CRT therapy. In this one-way communication example, the SICD may be configured to transmit communications to the LPD and the LPD may be configured to receive the communication from the SICD. Alternatively, one-way communication may be established such that the LPD may be configured to transmit communications to the SICD (e.g., communication from an LPD). In other examples, two-way communication may allow confirmation of a detected of a cardiac condition (e.g., ventricular dyssynchrony, tachyarrhythmia, bradycardia, etc.) prior to delivery of any therapy. Communication between the SD and the LPD is described in greater details in U.S. patent application Ser. No. 13/756,085 filed May 26, 2013 and entitled "Systems and methods for leadless pacing and shock therapy," which is incorporated herein by reference in its entirety.

One or more of the embodiments described herein may utilize far-field sensing to carry out cardiac resynchronization pacing. In some embodiments, one or more of the electrodes of a device may be used for far-field sensing of electrical activity in a different chamber. For example, a right atrial electrode or a tissue-piercing electrode may be used to monitor far-field electrical activity of the right ventricle. The far-field sensing may be particularly useful in cardiac resynchronization pacing as described above. Ascertaining RV timing may be used to tailor the timing of the LV pace for an individual patient to allow for fusion pacing (e.g., fusing RV and LV activation).

Figure 7:
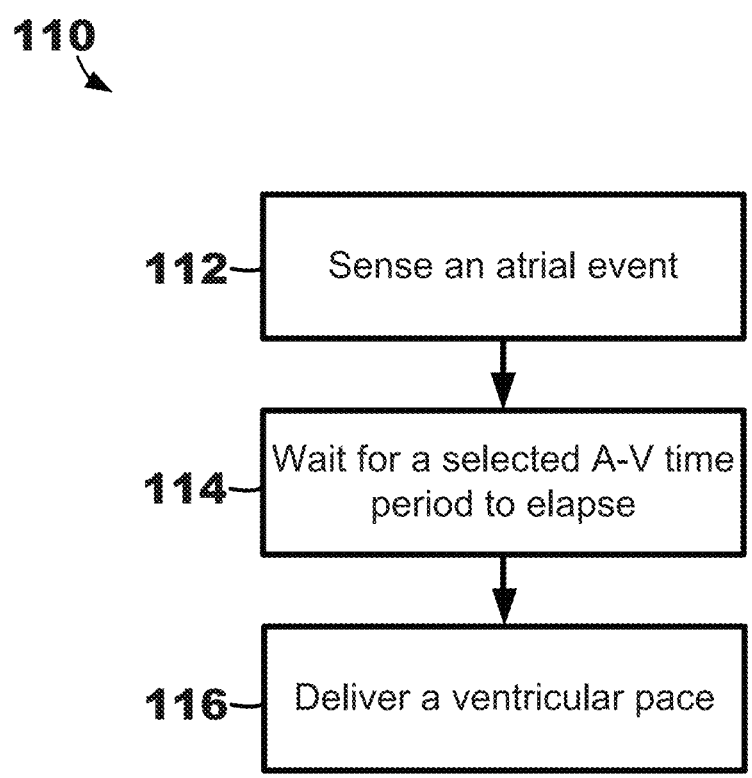
FIG. 7 is a flowchart of an illustrative pacing therapy method for use with, e.g., the illustrative method of FIG. 6.

FIG. 7 is a flowchart of a pacing therapy method 110 for use with, e.g., the method 100 of FIG. 6. For example, the method 110 may be used in process 104, which delivers pacing therapy to the ventricle. The method 110 may be described as an AV resynchronization therapy method.

The method 110 may include process 112, in which an atrial event is sensed. For example, the atrial event may be a right atrial event in monitored activity of the right atrium, e.g., as mentioned in process 102. The right atrial electrode may be used to sense the right atrial event within monitored electrical activity of the right atrium. In addition, or alternatively, the right atrial motion detector may be used to sense the right atrial event within monitored mechanical activity of the right atrium. The atrial event may be determined by the controller of the medical device using the sensing circuit.

The method 110 may further include process 114, which includes waiting for a selected A-V time period to elapse in response to the detection of the atrial event in process 112. For example, the controller of the medical device may wait the selected A-V time period after detecting the atrial event.

The method 110 may further include process 116, in which a ventricular pace is delivered in response to the atrial event after the selected A-V time period has elapsed in process 114. In some embodiments, process 116 may be performed without process 114. It is contemplated that the ventricular pace may be delivered in response to sensing the atrial event without using the selected A-V time period.

In some embodiments, the A-V time period is configured to synchronize an atrial event and a ventricular event for atrioventricular synchrony. The A-V time period may also be configured to, or modified to, improve cardiac resynchronization. For example, the A-V time period may be used to pace one or both ventricles for ventricular synchrony (e.g., using biventricular pacing or monoventricular pacing, such as fusion pacing) described herein in more detail below.

Figure 8:
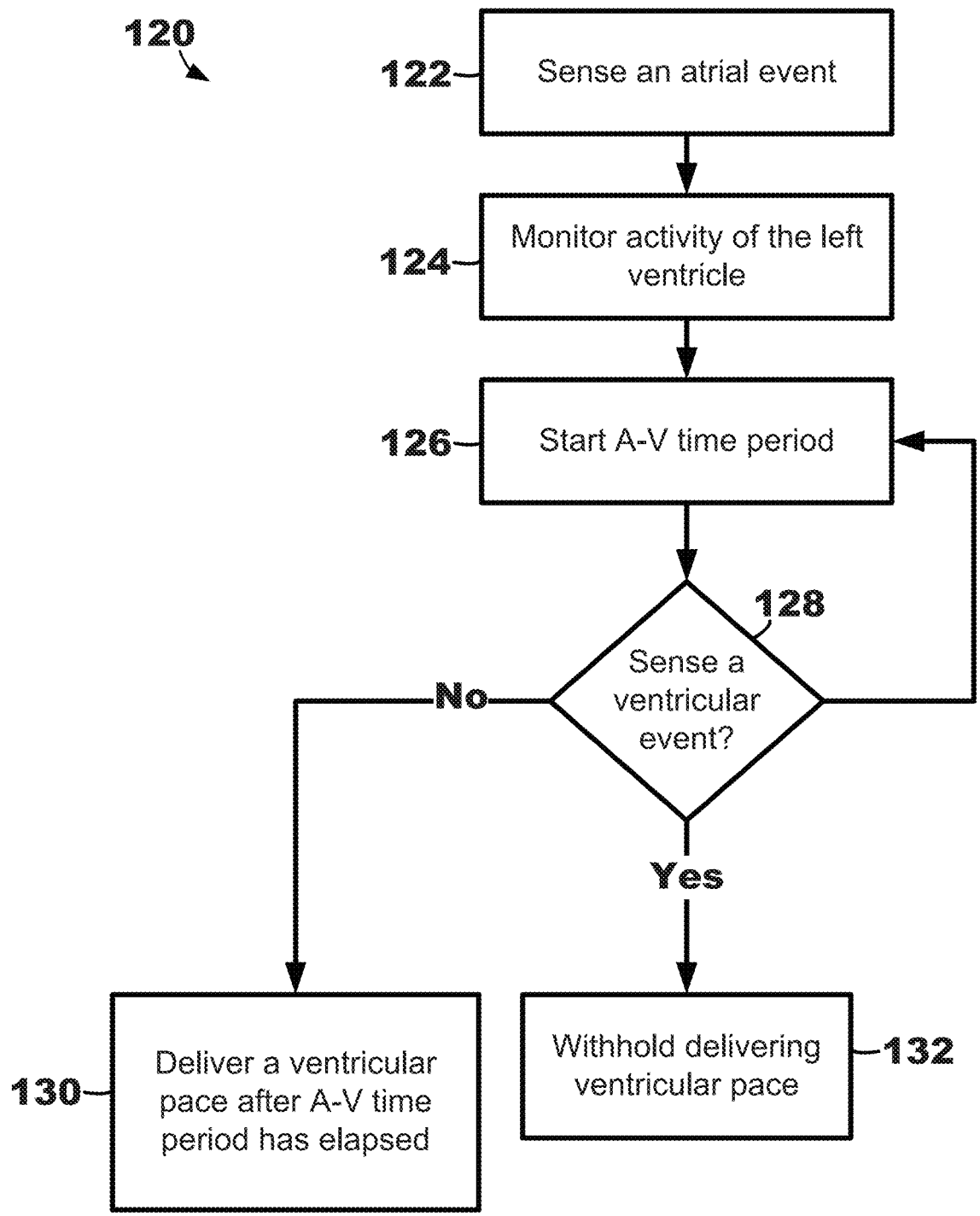
FIG. 8 is a flowchart of another illustrative pacing therapy method for use with, e.g., the illustrative method of FIG. 6.

FIG. 8 is a flowchart of another illustrative pacing therapy method 120 for use with, e.g., the method 100 of FIG. 6. For example, the method 120 may be used in process 104, which delivers pacing therapy to the ventricle. The method 120 may be described as an AV resynchronization therapy method.

The method 120 may include process 122, in which an atrial event is sensed within the monitored activity from process 102 (FIG. 6). Process 122 may be the same or similar to process 112 of method 110 (FIG. 7).

The method 120 may further include process 124, in which activity of the left ventricle is monitored. One or more tissue-piercing electrodes may be used to sense the activity of the left ventricle. If more than one tissue-piercing electrode has contact with LV myocardium, the tissue-piercing electrodes can be used to both sense and pace the LV.

The method 120 may further include process 126, which starts an A-V time period. The method 120 may further include process 128, which determines whether a ventricular event is sensed in response to the monitored activities in processes 122 and 124. In particular, the process 128 may determine whether a ventricular event is sensed before the A-V time period elapses. The controller of the medical device may be used to make the determination. If a ventricular event is not sensed in process 128, the method 120 may branch to process 130. If a ventricular event is sensed, the method 120 may branch to process 132.

The method 120 may further include process 130, in which a ventricular pace is delivered after the selected A-V time period has elapsed. Process 130 may be the same or similar to process 114 of method 110 (FIG. 7). The controller of the medical device may initiate or execute the ventricular pace using the therapy delivery circuit.

The method 120 may further include process 132, which withholds delivering the ventricular pace. Withholding the ventricular pace delivery may be described as inhibiting pacing therapy.

Figure 9:
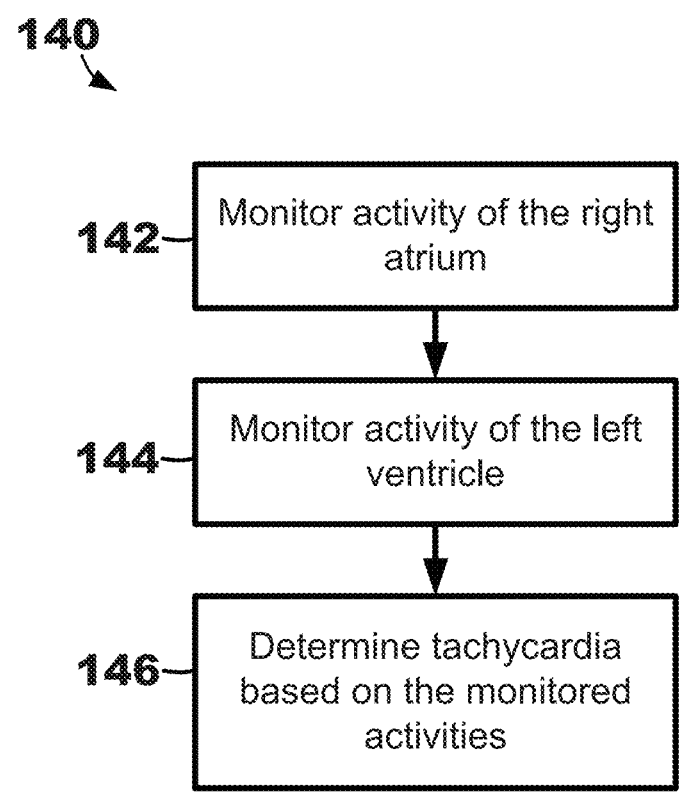
FIG. 9 is a flowchart of an illustrative tachycardia-related method for use with, e.g., the illustrative system and devices of FIGS. 1-5.

FIG. 9 is a flowchart of a tachycardia-related method 140 for use with, e.g., the system 2 of FIG. 1. For example, the method 140 may be used with the intracardiac medical device 10 (FIG. 1-2) or 710 (FIG. 5). The method 140 may be described as a tachycardia sensing method.

The method 140 may include process 142, in which activity of the right atrium is monitored. When implanted, the controller of the medical device may use the sensing circuit and right atrial electrode or right atrial motion detector to monitor the activity of the right atrium.

The method 140 may further include process 144, in which activity of the left ventricle is monitored. When implanted, the controller of the medical device may use the sensing circuit and tissue-piercing electrode, or a left ventricular motion detector, to monitor the activity of the left ventricle.

The method 140 may further include process 146, in which tachycardia is determined based on the monitored activities in processes 142 and 144. The controller may be used to make the determination.

Figure 10:
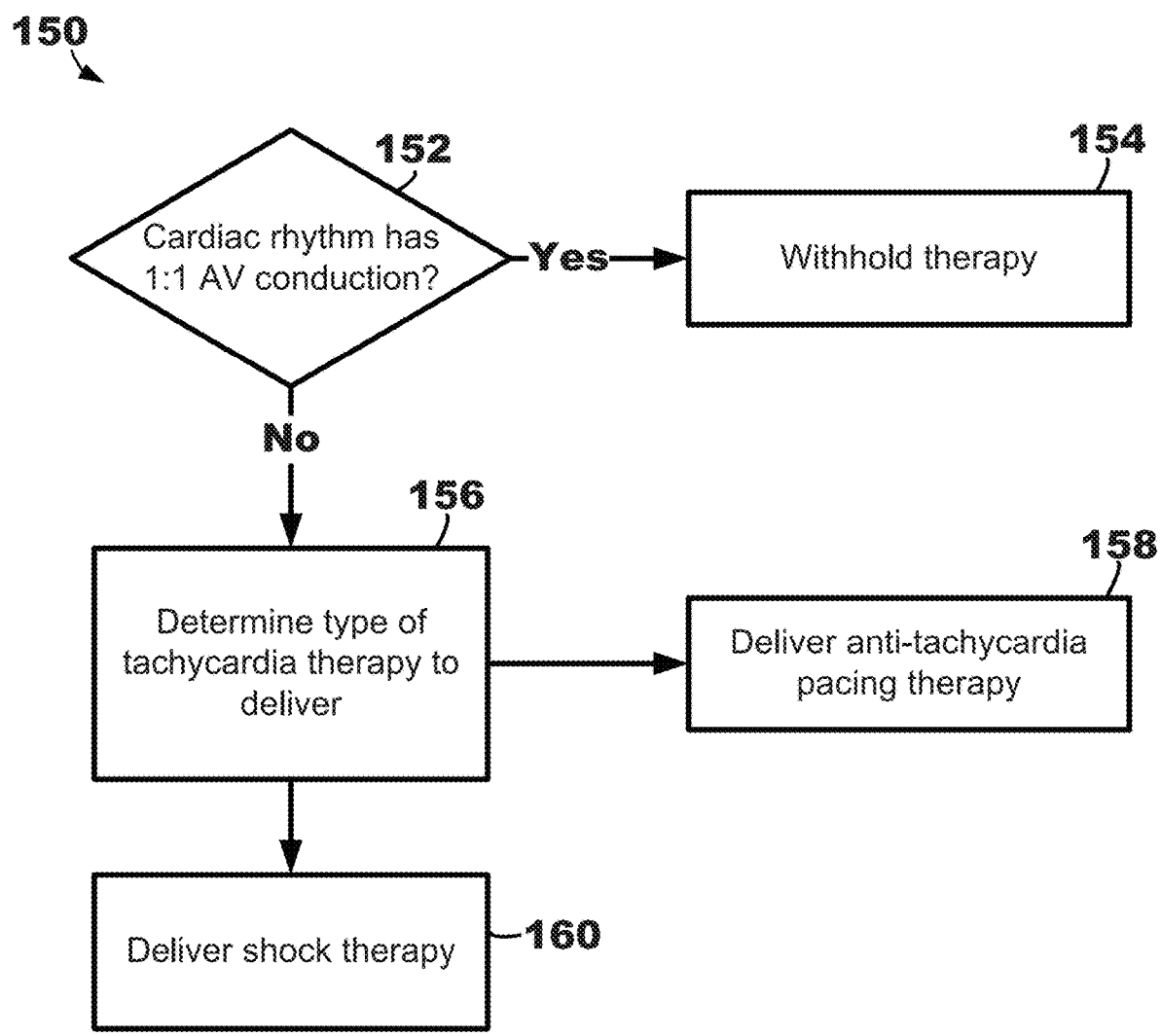
FIG. 10 is a flowchart of an illustrative tachycardia determination method for use with, e.g., the illustrative method of FIG. 9.

FIG. 10 is a flowchart of a tachycardia determination method 150 for use with, e.g., the method 140 of FIG. 9. For example, the method 150 may be used in process 146, which determines tachycardia based on the monitored activities. The method 150 may be described as a tachycardia classification method. A ventricular tachycardia event may be determined if the monitored V-rate exceeds a certain threshold (e.g., 120 bpm) or, additionally or alternatively, if the monitored intervals between successive V-events are less than a certain time-interval threshold (e.g., 500 ms).

The method 150 may include process 152, which determines whether a tachycardia rhythm has a 1:1 AV conduction rhythm or signature. As used herein, a 1:1 AV conduction or rhythm refers to every V-event being preceded by an A-event with a degree of regularity in terms of the A-V interval. The controller of the medical device may be used to make the determination. If a 1:1 AV conduction rhythm is determined, the method 150 may continue to process 154. If a 1:1 AV conduction rhythm is not determined by process 152, then the method 150 may continue to process 156.

The method 150 may further include process 154, in which therapy is withheld. For example, the controller may be used to withhold tachycardia-related therapy in response to determining that the detected rhythm is non-treatable.

The method 150 may further include process 156 (e.g., in response to not determining a 1:1 AV conduction rhythm in process 152), in which a type of tachycardia therapy to deliver is determined. For example, a determination may be made that the V-rate is faster than a rate threshold (e.g., 200 bpm) for ventricular fibrillation, in which case the device may initiate shock therapy in process 160. If not, then the device may initiate anti-tachycardia pacing therapy in process 158.

Figure 11:
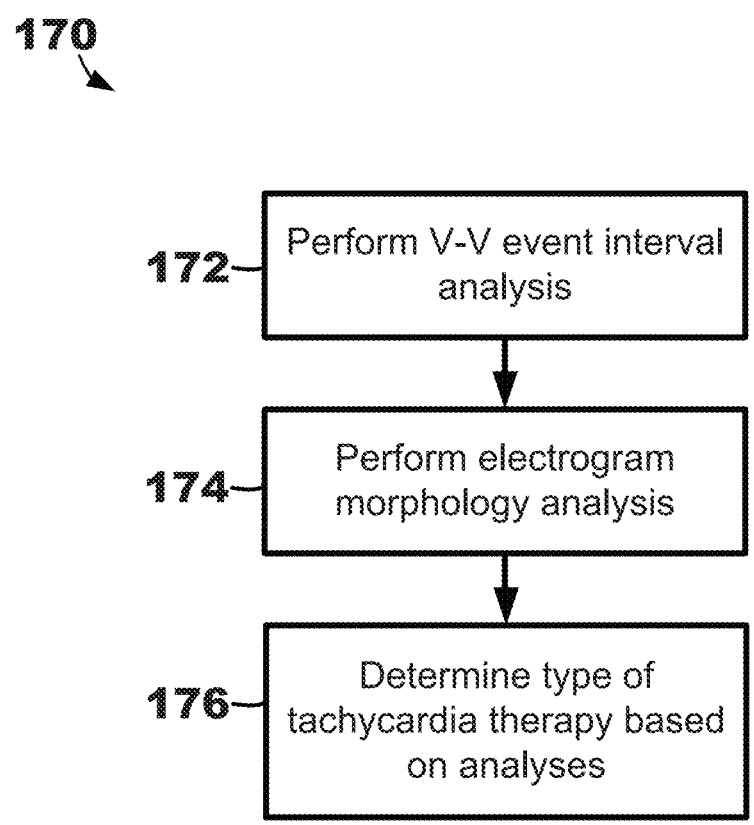
FIG. 11 is a flowchart of an illustrative tachycardia therapy determination method for use with, e.g., the illustrative method of FIG. 10.

FIG. 11 is a flowchart of a tachycardia therapy determination method 170 for use with, e.g., the method 150 of FIG. 10. For example, the method 170 may be used in process 156, which determines a type of tachycardia therapy to deliver.

The method 170 may include process 172, which performs a V-V event interval analysis, which includes determination of parameters like median, range, mode-sum, or other metrics reflective of how fast a tachycardia rhythm is and how regular is the interval between successive V-events. The method 170 may further include process 174, which performs electrogram morphology analysis. This may include comparing entire morphology or gross morphologic features of different V-events within a tachycardia rhythm and determining a morphologic similarity index. Details of determining morphologic and rate regularity of tachycardia events may be described in U.S. Pat. No. 8,594,775 (Ghosh et al.), which is incorporated herein by reference in its entirety.

The method 170 may further include process 176, in which rate and rhythm regularity of tachycardia events are determined based on combination of monitoring of intervals between successive V events (process 172) and corresponding electrogram morphologies (process 174). In some embodiments, a monomorphic VT may be determined based on regularity of the successive V-events and/or similarity of electrogram morphologies corresponding to the V-events, whereas a polymorphic rhythm may be determined if both rate regularity and morphology similarity criteria are not met.

Non-limiting examples of tachycardia therapy that may be delivered include anti-tachycardia pacing and shock therapy (e.g., defibrillation therapy). In some embodiments, if a monomorphic VT is determined, the device may initiate anti-tachycardia pacing (ATP). If a polymorphic rhythm is determined the device may initiate shock therapy by signaling the external device to deliver a shock.

Examples of tachycardia therapy determination methods, including interval analyses and electrogram morphology analyses, that may be used with the methods of the present disclosure may be described in U.S. Pat. No. 7,031,711 (Brown et al.), issued 18 Apr. 2016, and U.S. Pat. No. 8,594,775 (Ghosh et al.), issued 26 Nov. 2013, and U.S. Pat. No. 8,750,994 (Ghosh et al.), issued 10 Jun. 2014, each of which is incorporated herein by reference in its entirety.

Figure 12:
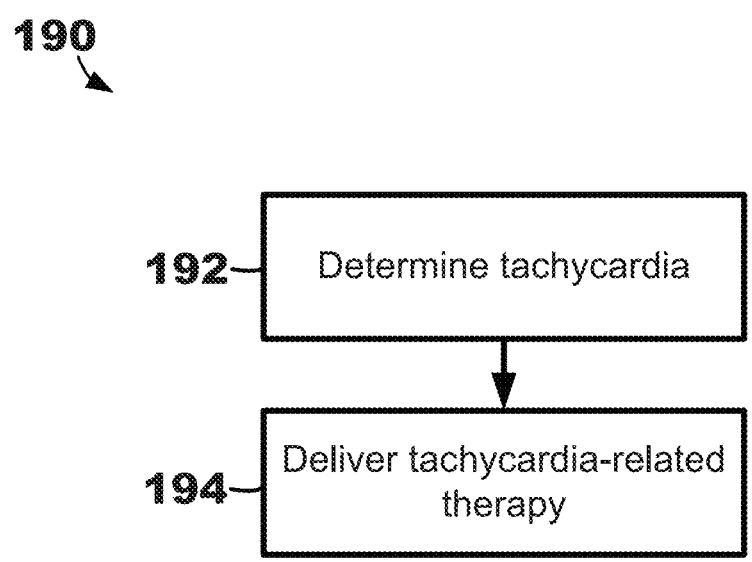
FIG. 12 is a flowchart of another illustrative anti-tachycardia method for use with, e.g., the illustrative system and devices of FIGS. 1-5.

FIG. 12 is a flowchart of an anti-tachycardia method 190 for use with, e.g., the system 2 of FIG. 1. For example, the method 190 may be used with the intracardiac medical device 10 and the separate medical device 50 (FIG. 1).

The method 190 may include process 192, which determines that tachycardia is present. For example, the controller of the medical device may determine that tachycardia is present based on monitored activities generated using the plurality of electrodes and/or one or more motion detectors. Process 192 may be the same or similar to process 146 of FIG. 9 or process 176 of FIG. 11.

The method 190 may further include process 194, which delivers tachycardia-related therapy using the medical device and/or separate medical device based on the determination that tachycardia is present in process 192. For example, the medical device may use one or more of the plurality of electrodes to provide anti-tachycardia pacing.

In some embodiments, another device may perform process 192 to determine whether tachycardia has been detected and the medical device may be used to perform process 194 to provide the tachycardia-related therapy.

Figure 13:
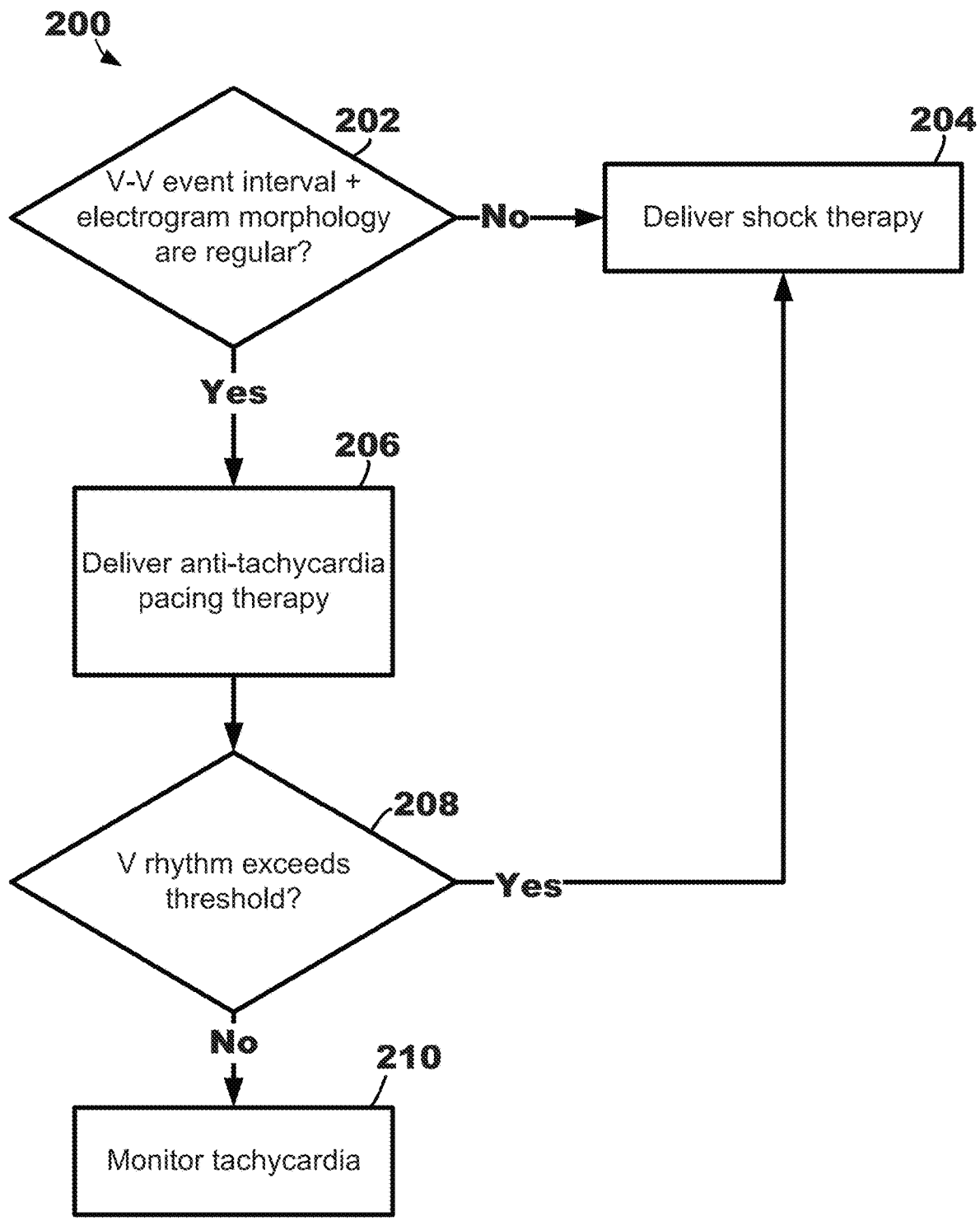
FIG. 13 is a flowchart of an illustrative tachycardia therapy delivery method for use with, e.g., the illustrative method of FIG. 12.

FIG. 13 is a flowchart of a tachycardia therapy delivery method 200 for use with, e.g., the method 190 of FIG. 12. For example, the method 200 may be included in process 194 of method 190, which delivers tachycardia-related therapy.

The method 200 may include process 202, which may be similar to process 176 of FIG. 11 that determines a type of tachycardia to deliver. In particular, process 202 may determine whether the V-V event interval (determined in process 172 of method 170) and the electrogram morphology (determined in process 174 of method 170) are both regular. If one or both are irregular, the method 200 may continue with process 204. If both are regular, the method 200 may continue with process 206.

The method 200 may further include process 204 to deliver shock therapy. Shock therapy may be initiated using the medical device. For example, the medical device may deliver a signaling pulse (e.g., a distinctive single, high-output pacing pulse to the ventricle) or other trigger. The pacing signal or other trigger may be detected by the separate medical device, which may provide the electrical shock.

The method 200 may further include process 206 to deliver anti-tachycardia pacing therapy (ATP). The ATP may be delivered using the plurality of electrodes of the medical device. After process 206, the method 200 may continue with process 208.

The method 200 may include process 208 to determine whether the V rhythm exceeds a threshold after ATP delivery has begun in process 206. In particular, a V rhythm threshold may be used to distinguish monomorphic VT from other types of tachycardia, in the same or similar manner as process 156 of method 150 (FIG. 10). If the V rhythm exceeds the V rhythm threshold, the method 200 may continue to process 204 described above. If the V rhythm does not exceed the V rhythm threshold, the method may continue with process 210.

The method may further include process 210 to monitor tachycardia. For example, process 210 may include performing the method 170 of FIG. 11. After process 210, the method 200 may return to process 202. While the V-V event interval and the electrogram morphology are regular, the method 200 may continue to loop, for example, unless shock therapy is delivered in process 204.

Figure 14:
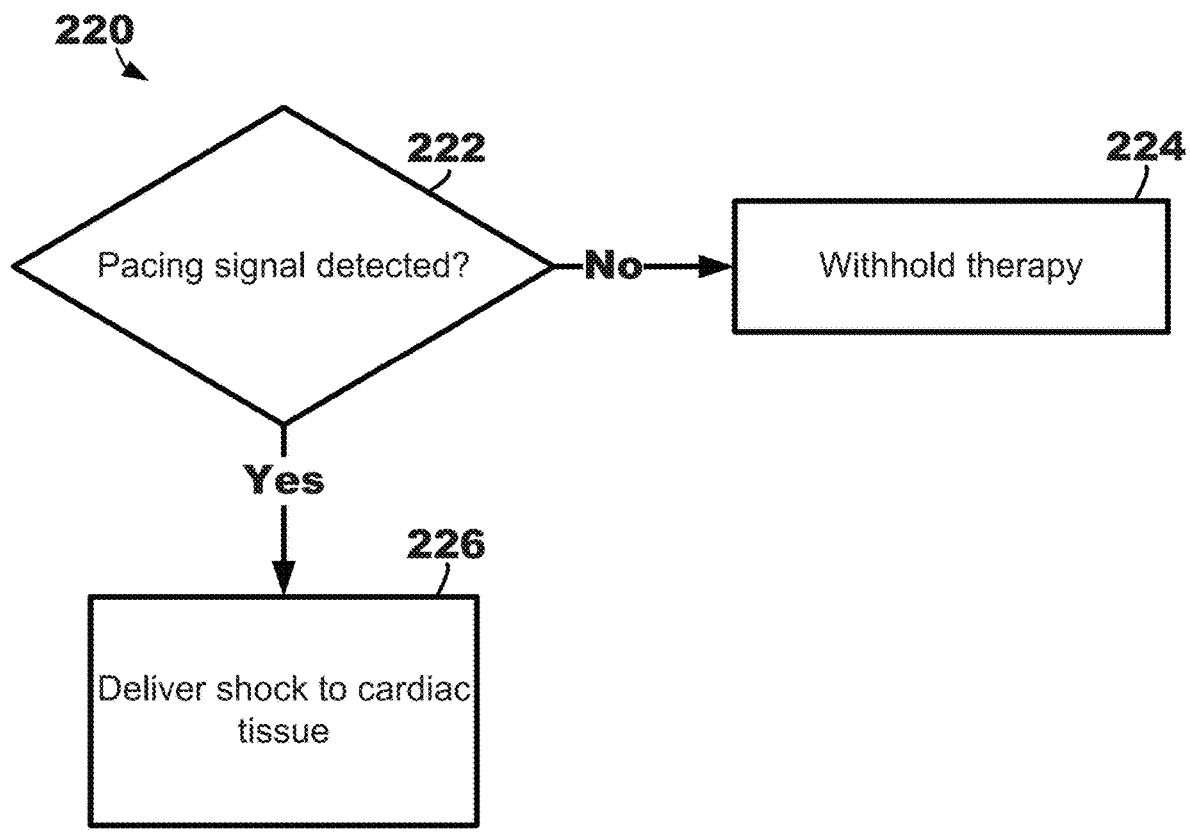
FIG. 14 is a flowchart of an illustrative shock therapy method for use with, e.g., the illustrative method of FIG. 13.

FIG. 14 is a flowchart of a shock therapy method 220 for use with, e.g., the method 200 of FIG. 13. For example, the method 220 may be included in process 204, which delivers shock therapy. The method 220 may be executed by the separate medical device 50 of FIG. 1.

The method 220 may begin with process 222, which determines whether a pacing signal has been detected. As described with respect to process 204 of FIG. 13, the medical device may provide a pacing signal, which may be detected by the separate medical device. If the pacing signal is not detected, the method 220 may continue to process 224. If the pacing signal is detected, the method 220 may continue with process 226.

The method 220 may further include process 224 to withhold therapy. In particular, process 224 may withhold shock therapy from being delivered by the separate medical device (e.g., extravascular ICD).

The method 220 may further include process 226 to deliver a shock to cardiac tissue of the patient's heart. In particular, the separate medical device may be used to provide the shock as, e.g., the medical device may not have a sufficient battery capacity, size, or positioning sufficient to deliver an effective cardioversion or defibrillation shock.

Figure 15:
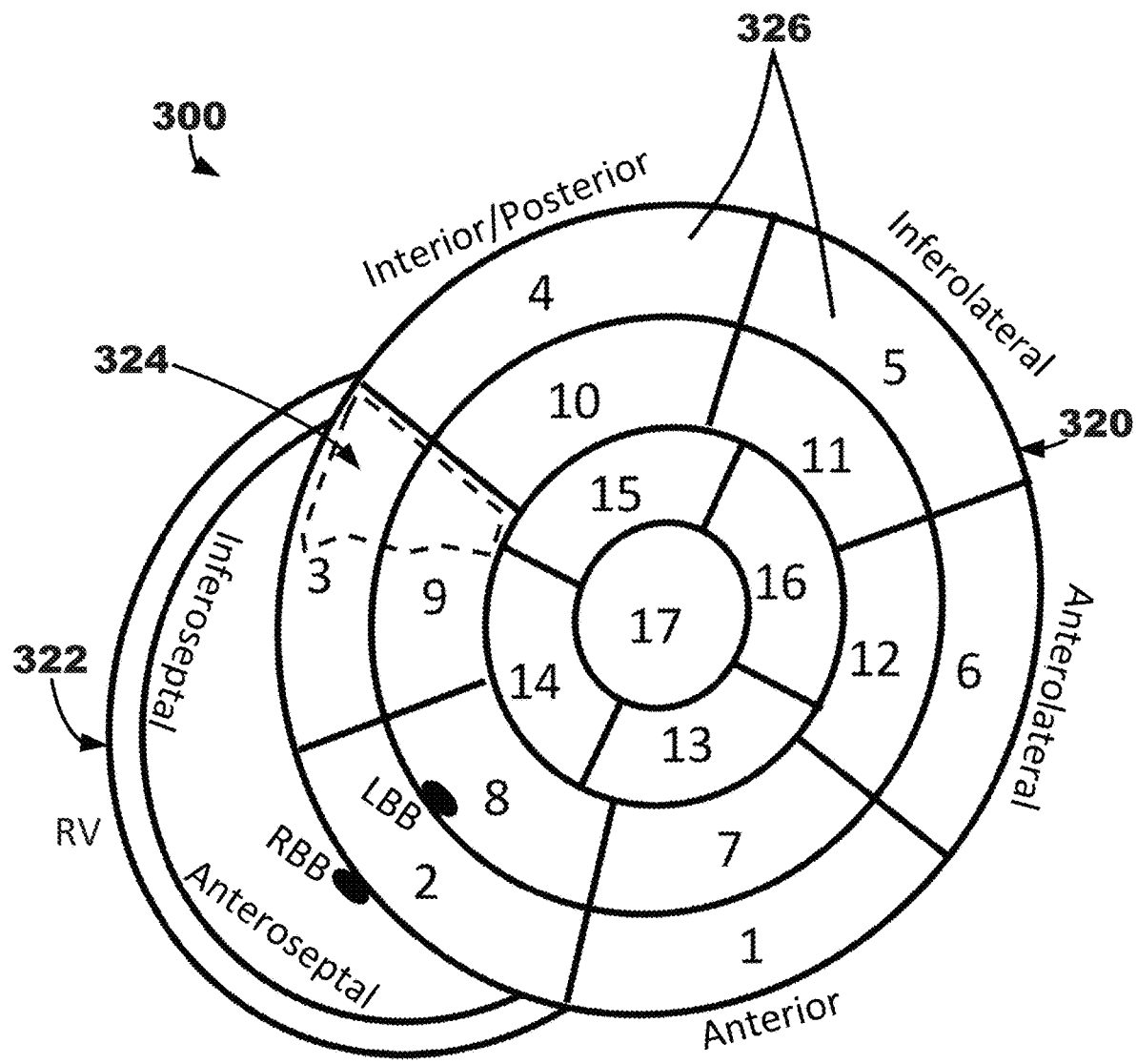
FIG. 15 is a conceptual diagram of a map of a patient's heart in a standard 17 segment view of the left ventricle showing various electrode implantation locations for use with, e.g., the exemplary system and devices of FIGS. 1-5.

FIG. 15 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) and left bundle branch (LBB).

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body.

Once implanted, the tissue-piercing electrode may be positioned in the target implant region 4 (FIG. 1), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of at least one of the basal inferoseptal area 3 and mid-inferoseptal area 9. For example, the high inferior/posterior basal septal region may include region 324 illustrated generally as a dashed-line boundary. As shown, the dashed line boundary represents an approximation of about where the high inferior/posterior basal septal region and may take somewhat different shape or size depending on the particular application. Without being bound by any particular theory, intraventricular synchronous pacing and/or activation may result from stimulating the high septal ventricular myocardium due to functional electrical coupling between the subendocardial Purkinje fibers and the ventricular myocardium.

Figure 16:
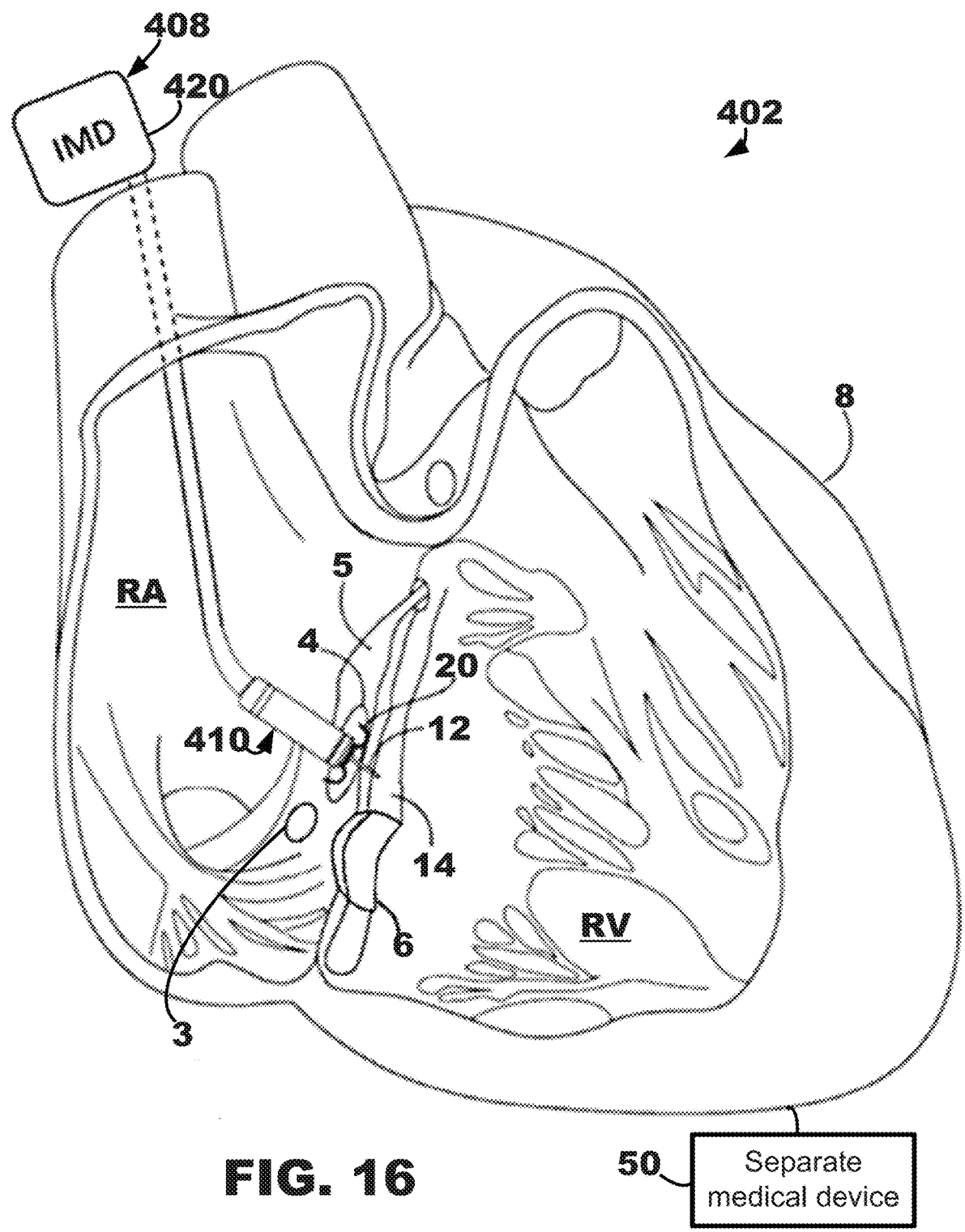
FIGS. 16-18 are conceptual diagrams of illustrative cardiac therapy systems including medical devices including leads with electrodes implanted in a patient's heart shown in a cross-sectional view for use with, e.g., the illustrative methods of FIGS. 6-14 or the illustrative system and devices of FIGS. 1-5.
Figure 17:
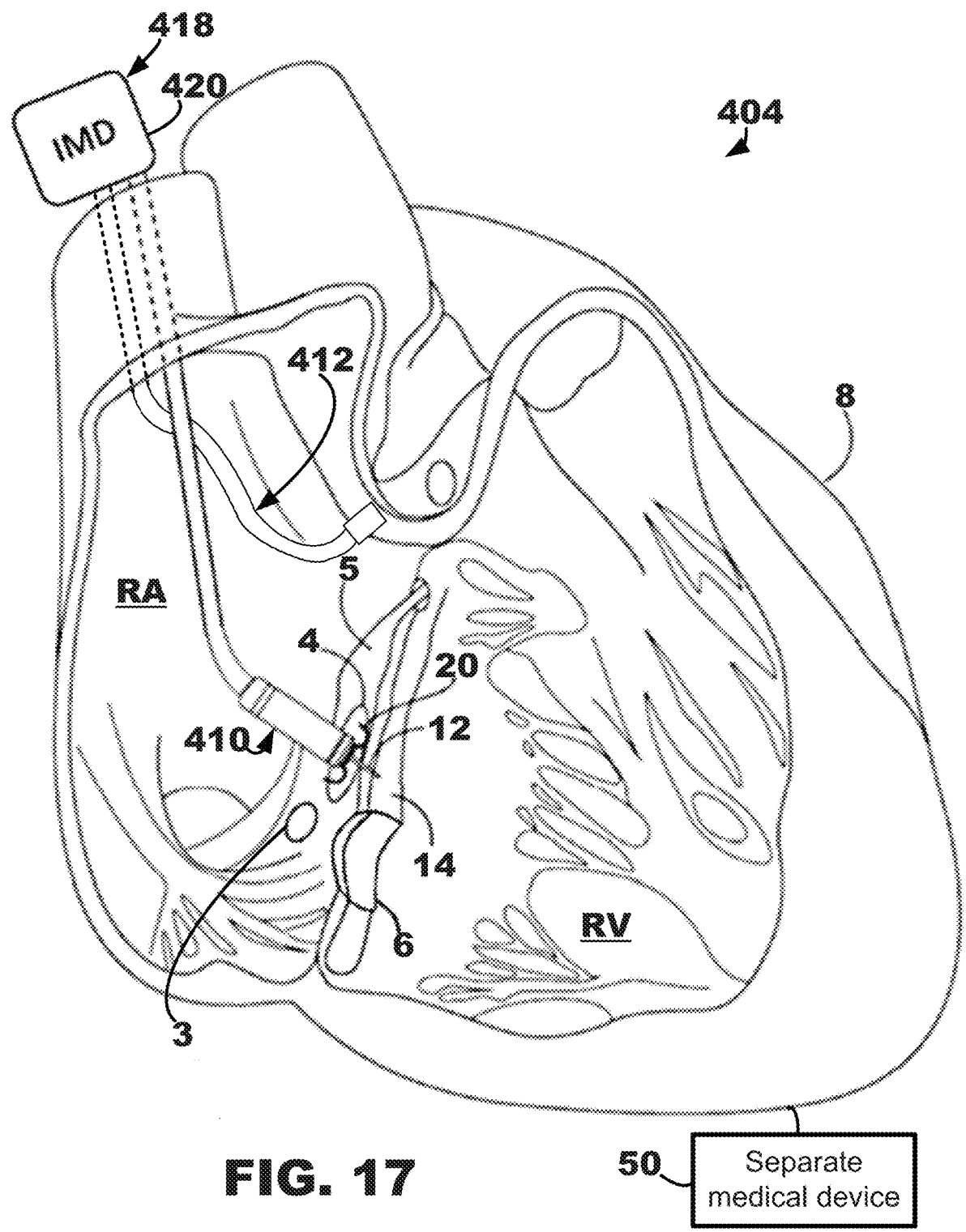
Figure 18:
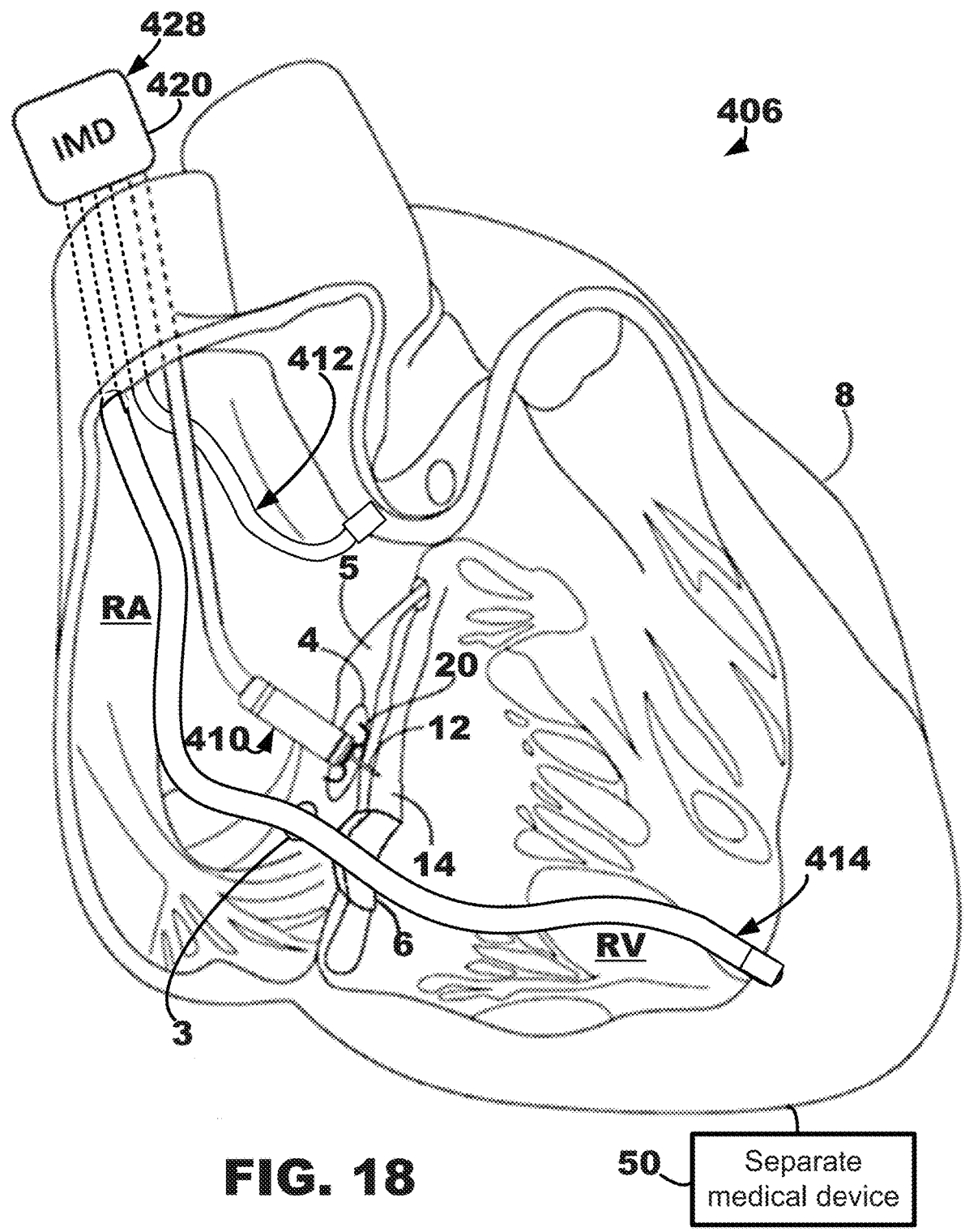

FIGS. 16-18 are conceptual diagrams of illustrative cardiac therapy systems 402, 404, 406 including leaded medical devices 408, 418, 428 with electrodes implanted in a patient's heart 8. Many of the structures of cardiac therapy systems 402, 404, 406 may be the same as those in cardiac therapy system 2. Accordingly, many of the structures depicted in FIGS. 16-18 have the same numbering as the structures depicted in FIG. 1. The description of some reference characters shown in FIGS. 16-18 (e.g., separate medical device 50) may be found in the description above, in particular, with respect to FIG. 1, and is not repeated here with reference to FIGS. 16-18.

With reference to FIG. 16, leaded medical device 408 includes one, or a single, implantable lead 410 having a tissue-piercing electrode 12 coupled to a distal end region of the lead and implanted inside the patient's heart 8. The housing 420 of the leaded medical device 408 may be implanted and positioned outside of the patient's heart 8. The lead 410 may include a right atrial electrode, and the device 408 may operate as a dual-channel capable device. In some embodiments, the lead 410 may not include a right atrial electrode. In other words, the leaded medical device 408 may be a single channel device, which may be used for asynchronous, triggered, or other single channel pacing. For example, lead 410 may sense activity or deliver pacing to the left ventricle (LV) when the tissue-piercing electrode 12 is implanted as described above (e.g., with respect to map 300 of FIG. 15 and with respect to device 10 of FIG. 1).

With reference to FIG. 17, leaded medical device 418 is like leaded medical device 408 except that device 418 includes two implantable leads 410, 412. In particular, implantable lead 412 may include an electrode (e.g., a right atrial electrode) coupled to a distal end region of the lead and may be implanted in a different location than lead 410. In some embodiments, lead 412 is implanted in a different region of the right atrium. In some embodiments, each lead 410, 412 may contribute one channel of a dual-channel device 418. For example, lead 410 may sense activity or deliver pacing to the left ventricle (LV), and lead 412 may sense activity or deliver pacing to the right atrium (RA).

With reference to FIG. 18, leaded medical device 428 is like leaded medical device 418 except that device 428 includes three implantable leads 410, 412, 414. In particular, implantable lead 414 may include an electrode (e.g., a right ventricular electrode) coupled to a distal end region of the lead and may be implanted in a different location than leads 410, 412. In some embodiments, lead 414 is implanted in a region of the right ventricle. In some embodiments, each lead 410, 412, 414 may contribute one channel to a multi-channel device 428. For example, lead 410 may sense activity or deliver pacing to the left ventricle (LV), lead 412 may sense activity of deliver pacing to the right atrium (RA), and lead 414 may sense activity or deliver pacing to the right ventricle (RV).

Figure 19:
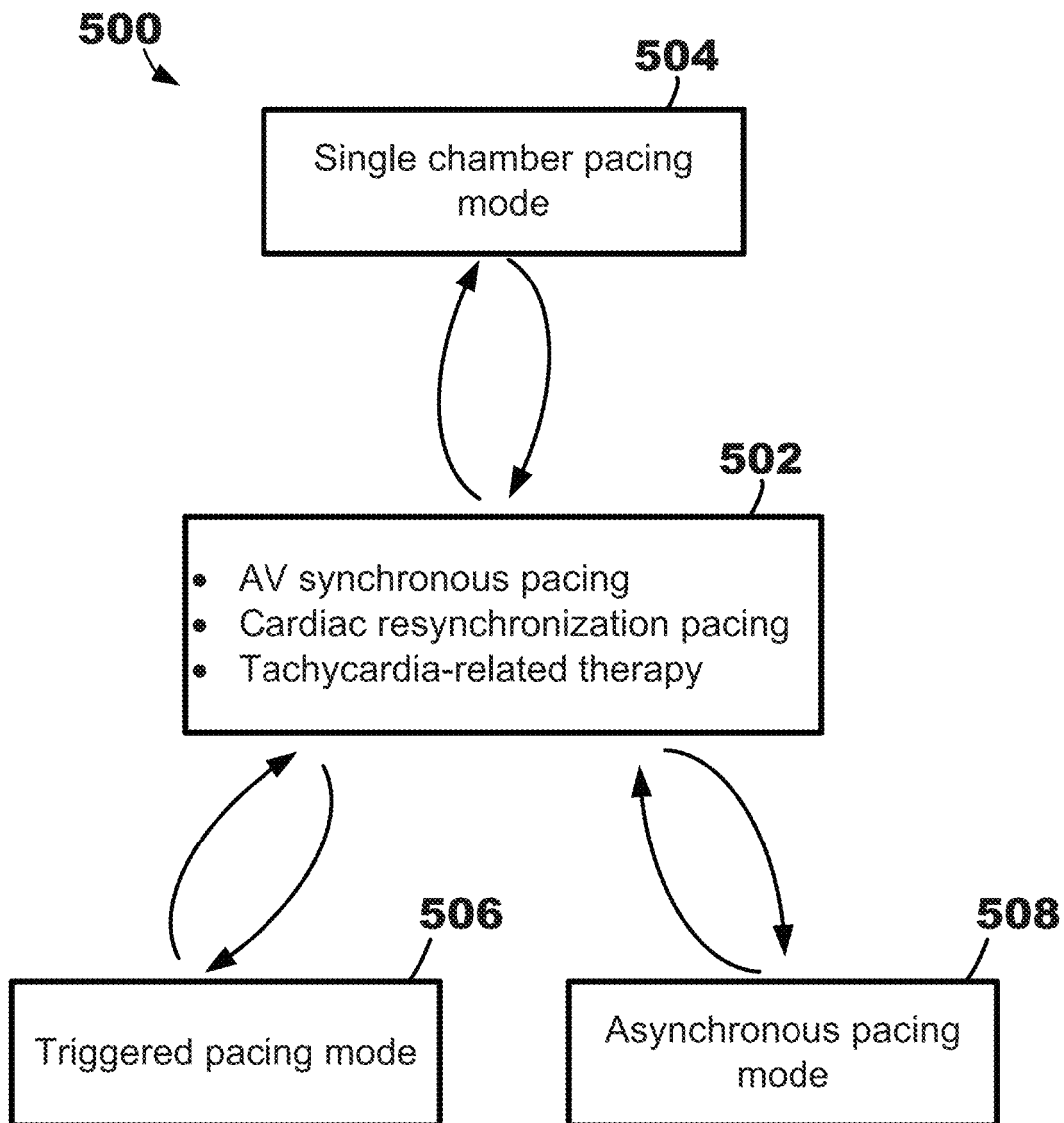
FIG. 19 is a state diagram showing different illustrative modes for use with, e.g., the illustrative systems and devices of FIGS. 1-5 and FIGS. 16-18.

FIG. 19 is a state diagram 500 showing different illustrative therapy modes that the implantable medical device and systems described herein may initiate or enter during operation. Such implantable medical devices and systems may have a nominal state 502, in which the device is configured to perform at least one or more of atrioventricular synchronous pacing, cardiac resynchronization pacing, and tachycardia-related therapy. The device may initiate or switch to a single chamber pacing mode in state 504 in response to detecting atrial fibrillation. Atrial fibrillation may be detected by the device or by a separate device. The device may return to the nominal state 502 from state 504.

The device may initiate or switch to a triggered pacing mode in state 506, in which the device delivers pacing in response to a trigger (e.g., pacing signal) from a separate device (e.g., an ICD). In some embodiments, the implantable medical device may include only electrodes to pace the LV (e.g., tissue-piercing electrode), which is triggered by a separate, or remote, device (e.g., a subcutaneous or leaded device) that determines timing and sends a command or trigger to the implantable medical device to pace the LV to deliver CRT. The device may return to the nominal state 502 from state 506.

Further, the device may initiate or switch to an asynchronous pacing mode in state 508, in which the device delivers pacing independent of sensing in other chambers. The device may return to the nominal state 502 from state 508.

Figure 20:
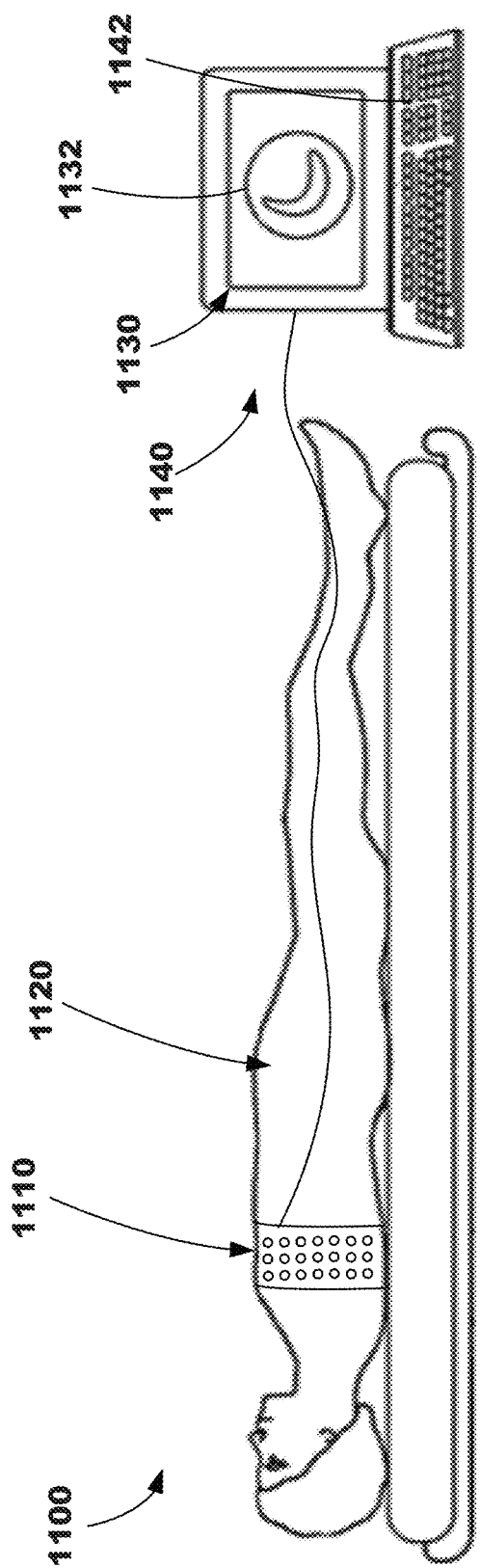
FIG. 20 is a diagram of an illustrative system including electrode apparatus, display apparatus, and computing apparatus for use with, e.g., the illustrative systems and devices of FIGS. 1-5 and FIGS. 16-18.
Figure 21:
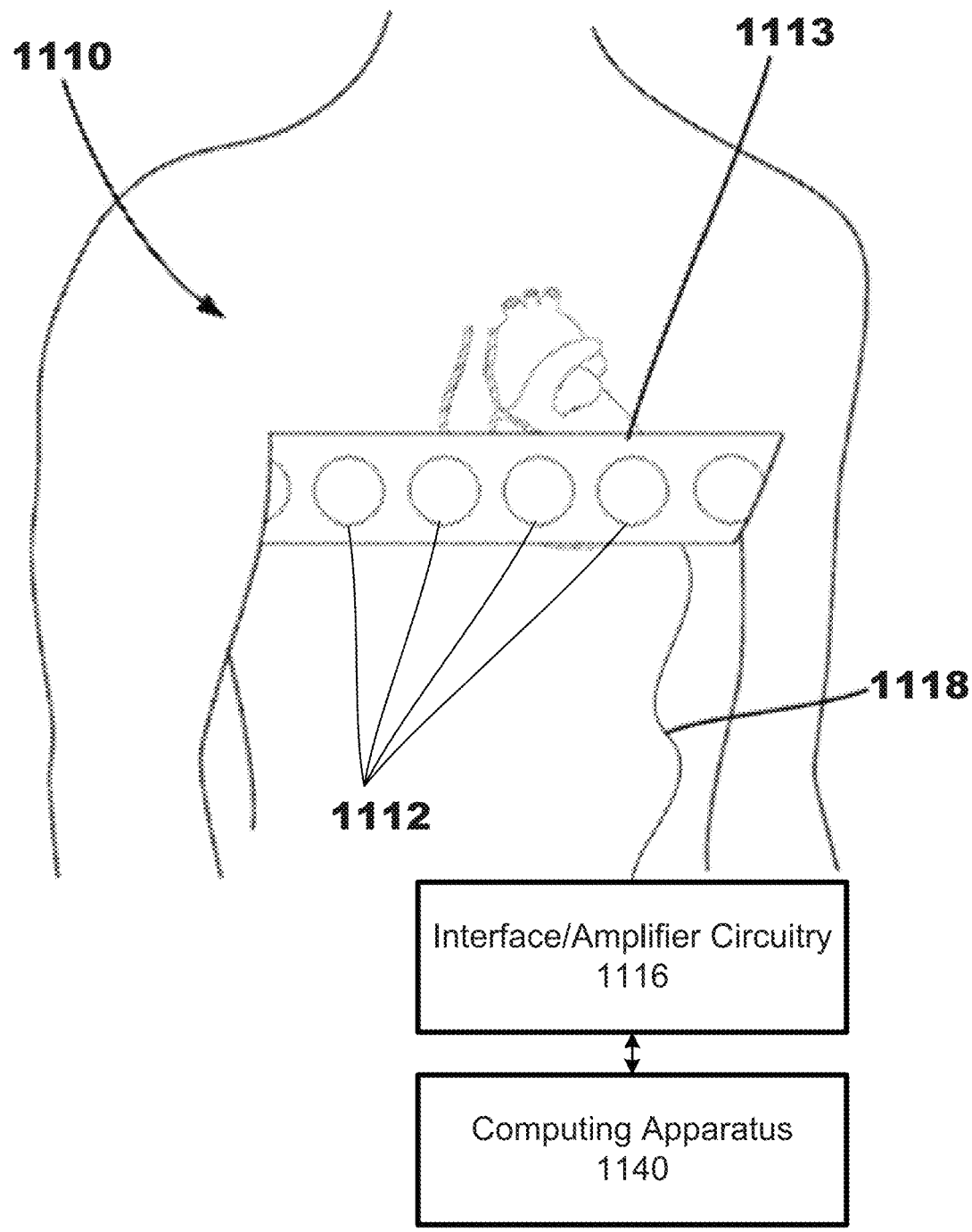
FIGS. 21-22 are diagrams of illustrative external electrode apparatus for measuring torso-surface potentials for use with, e.g., the illustrative systems and devices of FIGS. 1-5 and FIGS. 16-18.
Figure 22:
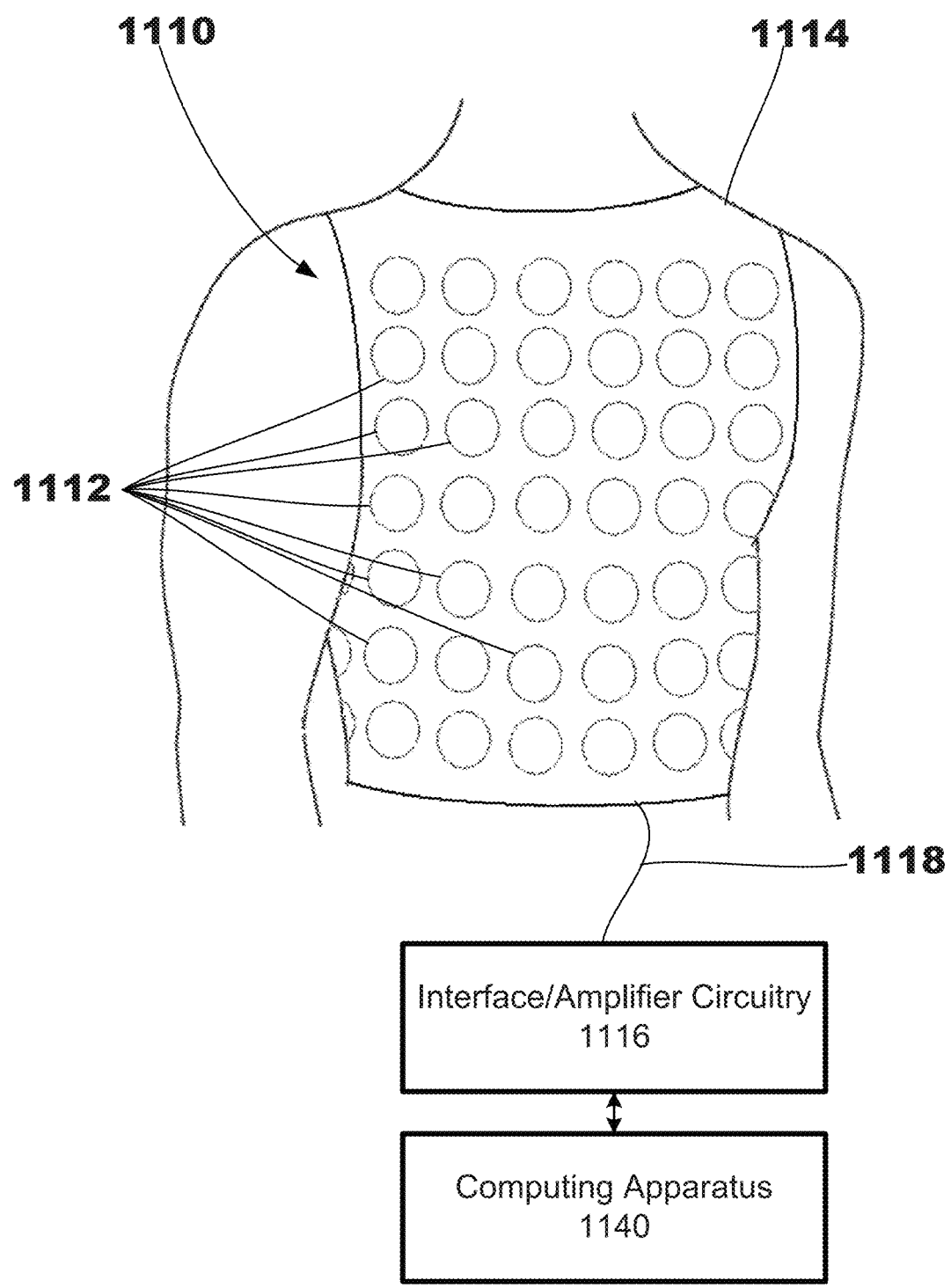

Reference will now be made to FIGS. 20-22, which are diagrams of illustrative systems include electrode apparatus. An illustrative system 1100 including electrode apparatus 1110, display apparatus 1130, and computing apparatus 1140 is depicted in FIG. 20. The electrode apparatus 1110 as shown includes a plurality of electrodes incorporated, or included, within a band wrapped around the chest, or torso, of a patient 1120. The electrode apparatus 1110 is operatively coupled to the computing apparatus 1140 (e.g., through one or wired electrical connections, wirelessly, etc.) to provide electrical signals from each of the electrodes to the computing apparatus 1140 for analysis, evaluation, etc. Illustrative electrode apparatus may be described in U.S. Pat. No. 9,320,446 entitled "Bioelectric Sensor Device and Methods" and issued on Apr. 26, 2016, which is incorporated herein by reference in its entirety. Further, illustrative electrode apparatus 1110 will be described in more detail in reference to FIGS. 21-22.

Although not described herein, the illustrative system 1100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to locate and position a device to deliver VfA cardiac pacing therapy and/or to locate or select a pacing electrode or pacing vector proximate the patient's heart for Ventricle from atrium pacing therapy in conjunction with the evaluation of Ventricle from atrium pacing therapy.

For example, the illustrative systems, methods, and interfaces may provide image guided navigation that may be used to navigate leads including leadless devices, electrodes, leadless electrodes, wireless electrodes, catheters, etc., within the patient's body while also providing noninvasive cardiac therapy evaluation including determining whether a ventricle from atrium (VfA) paced setting is acceptable or determining whether one or more selected parameters are acceptable, such as selected location information (e.g., location information for the electrodes to target a particular location in the left ventricle). Illustrative systems and methods that use imaging apparatus and/or electrode apparatus may be described in U.S. Patent Publication No. 2014/0371832 filed on Jun. 12, 2013 and entitled "Implantable Electrode Location Selection," U.S. Patent Publication No. 2014/0371833 filed on Jun. 12, 2013 and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical Electrical Vectors," each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MM, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the left ventricle, including a selected location within the high posterior basal septal area of the left ventricular cavity) within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 1130 and the computing apparatus 1140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 1110. In at least one embodiment, the computing apparatus 1140 may be a server, a personal computer, or a tablet computer. The computing apparatus 1140 may be configured to receive input from input apparatus 1142 and transmit output to the display apparatus 1130. Further, the computing apparatus 1140 may include data storage that may allow for access to processing programs or routines and/or one or more other types of data, e.g., for driving a graphical user interface configured to noninvasively assist a user in targeting placement of a pacing device and/or evaluating pacing therapy at that location (e.g., the location of an implantable electrode used for pacing, the location of pacing therapy delivered by a particular pacing vector, etc.).

The computing apparatus 1140 may be operatively coupled to the input apparatus 1142 and the display apparatus 1130 to, e.g., transmit data to and from each of the input apparatus 1142 and the display apparatus 1130. For example, the computing apparatus 1140 may be electrically coupled to each of the input apparatus 1142 and the display apparatus 1130 using, e.g., analog electrical connections, digital electrical connections, wireless connections, bus-based connections, network-based connections, internet-based connections, etc. As described further herein, a user may provide input to the input apparatus 1142 to manipulate, or modify, one or more graphical depictions displayed on the display apparatus 1130 and to view and/or select one or more pieces of information related to the cardiac therapy.

Although as depicted the input apparatus 1142 is a keyboard, it is to be understood that the input apparatus 1142 may include any apparatus capable of providing input to the computing apparatus 1140 to perform the functionality, methods, and/or logic described herein. For example, the input apparatus 1142 may include a mouse, a trackball, a touchscreen (e.g., capacitive touchscreen, a resistive touchscreen, a multi-touch touchscreen, etc.), etc. Likewise, the display apparatus 1130 may include any apparatus capable of displaying information to a user, such as a graphical user interface 1132 including cardiac information, textual instructions, graphical depictions of electrical activation information, graphical depictions of anatomy of a human heart, images or graphical depictions of the patient's heart, graphical depictions of a leadless and/or leaded pacing device being positioned or placed to provide VfA pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 1130 may include a liquid crystal display, an organic light-emitting diode screen, a touchscreen, a cathode ray tube display, etc.

The processing programs or routines stored and/or executed by the computing apparatus 1140 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more illustrative methods and/or processes described herein. Data stored and/or used by the computing apparatus 1140 may include, for example, electrical signal/waveform data from the electrode apparatus 1110, dispersions signals, windowed dispersions signals, parts or portions of various signals, electrical activation times from the electrode apparatus 1110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system.

Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and/or interfaces may be implemented using a computer readable storage medium, configured with a computer program, where the storage medium so configured causes the computer to operate in a specific and predefined manner to perform functions described herein. Further, in at least one embodiment, the illustrative systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 1140 may be, for example, any fixed or mobile computer system (e.g., a controller, a microcontroller, a personal computer, minicomputer, tablet computer, etc.) and may be generally described as including processing circuitry. The exact configuration of the computing apparatus 1140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 1140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Electrical activation times of the patient's heart may be useful to evaluate a patient's cardiac condition and/or ventricle from atrium (VfA) cardiac therapy being delivered to a patient. Surrogate electrical activation information or data of one or more regions of a patient's heart may be monitored, or determined, using electrode apparatus 1110 as shown in FIG. 20 and in FIGS. 21-22. The illustrative electrode apparatus 1110 may be configured to measure body-surface potentials of a patient 1120 and, more particularly, torso-surface potentials of a patient 1120. As shown in FIG. 21, the illustrative electrode apparatus 1110 may include a set, or array, of electrodes 1112, a strap 1113, and interface/amplifier circuitry 1116. In at least one embodiment, a portion of the set of electrodes may be used wherein the portion corresponds to a particular location on the patient's heart. The electrodes 1112 may be attached, or coupled, to the strap 1113 and the strap 1113 may be configured to be wrapped around the torso of a patient 1120 such that the electrodes 1112 surround the patient's heart. As further illustrated, the electrodes 1112 may be positioned around the circumference of a patient 1120, including the posterior, lateral, posterolateral, anterolateral, and anterior locations of the torso of a patient 1120.

Further, the electrodes 1112 may be electrically connected to interface/amplifier circuitry 1116 via wired connection 1118. The interface/amplifier circuitry 1116 may be configured to amplify the signals from the electrodes 1112 and provide the signals to the computing apparatus 1140. Other illustrative systems may use a wireless connection to transmit the signals sensed by electrodes 1112 to the interface/amplifier circuitry 1116 and, in turn, the computing apparatus 1140, e.g., as channels of data. For example, the interface/amplifier circuitry 1116 may be electrically coupled to each of the computing apparatus 1140 and the display apparatus 1130 using, e.g., analog electrical connections, digital electrical connections, wireless connections, bus-based connections, network-based connections, internet-based connections, etc.

Although in the example of FIG. 21 the electrode apparatus 1110 includes a strap 1113, in other examples any of a variety of mechanisms, e.g., tape or adhesives, may be employed to aid in the spacing and placement of electrodes 1112. In some examples, the strap 1113 may include an elastic band, strip of tape, or cloth. In other examples, the electrodes 1112 may be placed individually on the torso of a patient 1120. Further, in other examples, electrodes 1112 (e.g., arranged in an array) may be part of, or located within, patches, vests, and/or other manners of securing the electrodes 1112 to the torso of the patient 1120.

The electrodes 1112 may be configured to surround the heart of the patient 1120 and record, or monitor, the electrical signals associated with the depolarization and repolarization of the heart after the signals have propagated through the torso of a patient 1120. Each of the electrodes 1112 may be used in a unipolar configuration to sense the torso-surface potentials that reflect the cardiac signals. The interface/amplifier circuitry 1116 may also be coupled to a return or indifferent electrode (not shown) that may be used in combination with each electrode 1112 for unipolar sensing. In some examples, there may be about 12 to about 50 electrodes 1112 spatially distributed around the torso of patient. Other configurations may have more or fewer electrodes 1112.

The computing apparatus 1140 may record and analyze the electrical activity (e.g., torso-surface potential signals) sensed by electrodes 1112 and amplified/conditioned by the interface/amplifier circuitry 1116. The computing apparatus 1140 may be configured to analyze the signals from the electrodes 1112 to provide as anterior and posterior electrode signals and surrogate cardiac electrical activation times, e.g., representative of actual, or local, electrical activation times of one or more regions of the patient's heart as will be further described herein. The computing apparatus 1140 may be configured to analyze the signals from the electrodes 1112 to provide as anterior-septal electrode signals and surrogate cardiac electrical activation times, e.g., representative of actual, or local, electrical activation times of one or more anterior-septal regions of the patient's heart, as will be further described herein, e.g., for use in evaluation of VfA pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 1140 may be configured to provide graphical user interfaces depicting the surrogate electrical activation times obtained using the electrode apparatus 1110. Illustrative systems, methods, and/or interfaces may noninvasively use the electrical information collected using the electrode apparatus 1110 to evaluate a patient's cardiac condition and/or ventricle from atrium pacing therapy being delivered to the patient.

FIG. 22 illustrates another illustrative electrode apparatus 1110 that includes a plurality of electrodes 1112 configured to surround the heart of the patient 1120 and record, or monitor, the electrical signals associated with the depolarization and repolarization of the heart after the signals have propagated through the torso of the patient 1120. The electrode apparatus 1110 may include a vest 1114 upon which the plurality of electrodes 1112 may be attached, or to which the electrodes 1112 may be coupled. In at least one embodiment, the plurality, or array, of electrodes 1112 may be used to collect electrical information such as, e.g., surrogate electrical activation times. Similar to the electrode apparatus 1110 of FIG. 21, the electrode apparatus 1110 of FIG. 22 may include interface/amplifier circuitry 1116 electrically coupled to each of the electrodes 1112 through a wired connection 1118 and be configured to transmit signals from the electrodes 1112 to computing apparatus 1140. As illustrated, the electrodes 1112 may be distributed over the torso of a patient 1120, including, for example, the anterior, lateral, posterolateral, anterolateral, and posterior surfaces of the torso of the patient 1120.

The vest 1114 may be formed of fabric with the electrodes 1112 attached to the fabric. The vest 1114 may be configured to maintain the position and spacing of electrodes 1112 on the torso of the patient 1120. Further, the vest 1114 may be marked to assist in determining the location of the electrodes 1112 on the surface of the torso of the patient 1120. In one or more embodiments, the vest 1114 may include 17 or more anterior electrodes positionable proximate the anterior torso of the patient, and 39 or more posterior electrodes positionable proximate the anterior torso of the patient. In some examples, there may be about 25 electrodes 1112 to about 256 electrodes 1112 distributed around the torso of the patient 1120, though other configurations may have more or less electrodes 1112.

As described herein, the electrode apparatus 1110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 1112, and not the entire set, can be used to generate activation times corresponding to a particular location of the patient's heart that the portion of the set of electrodes corresponds to.

The illustrative systems, methods, and interfaces may be used to provide noninvasive assistance to a user in the evaluation of a patient's cardiac health or status, and/or the evaluation of cardiac therapy such as ventricle from atrium (VfA) pacing therapy by use of the electrode apparatus 1110 (e.g., cardiac therapy being presently-delivered to a patient during implantation or after implantation). Further, the illustrative systems, methods, and interfaces may be used to assist a user in the configuration of the cardiac therapy, such as VfA pacing therapy, being delivered to a patient.

VfA pacing can be described as providing a synchronized homogeneous activation of ventricles of the heart. As an example, patients with atrial-ventricular (AV) block or prolonged AV timings that can lead to heart failure who have otherwise intact (e.g., normal) QRS can benefit from VfA pacing therapy. In addition, as an example, VfA pacing may provide beneficial activation for heart failure patients with intrinsic ventricular conduction disorders. Further, proper placement of VfA pacing can provide optimal activation of the ventricles for such patients. Further, left ventricular (LV) resynchronization for heart failure patients with left bundle branch block (LBBB) may find that VfA pacing enables easier access to left ventricular endocardium without exposing the leadless device or lead to endocardial blood pool. At the same time, in that example, this can help engage part of the conduction system to potentially correct LBBB and effectively resynchronize the patient.

Figure 23:
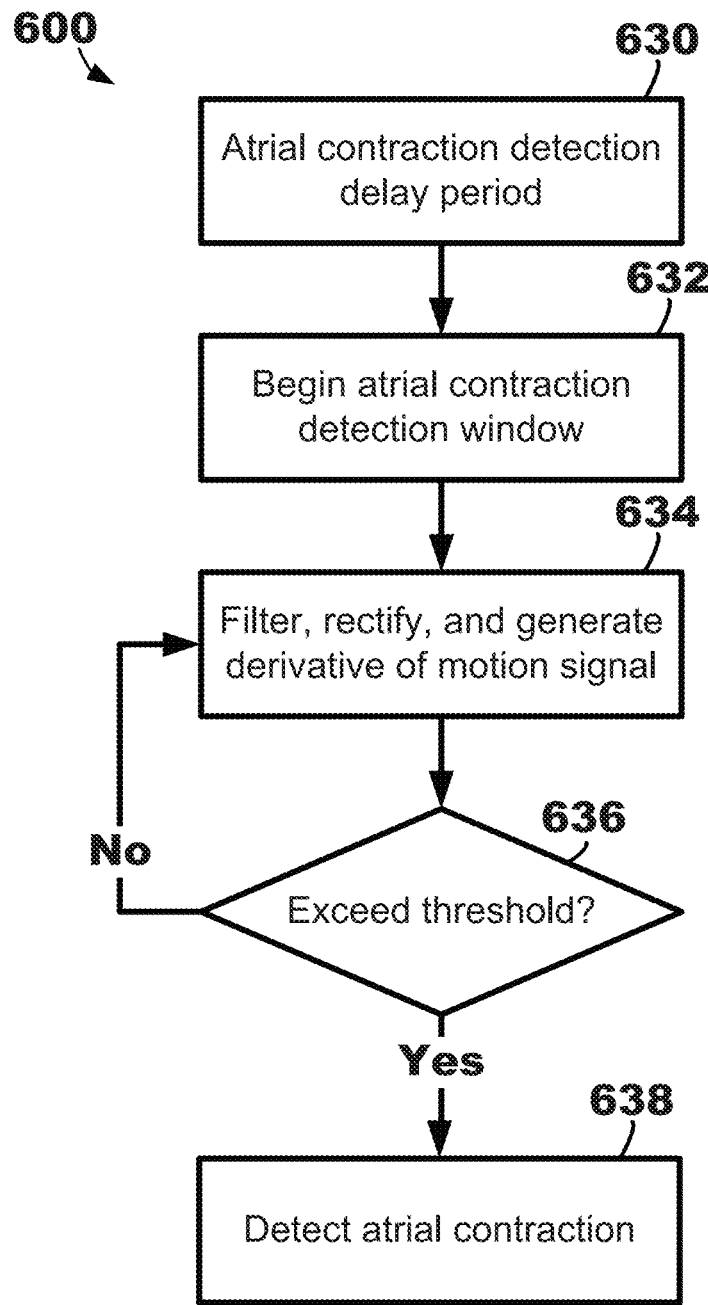
FIG. 23 is a flowchart of an illustrative method of detecting atrial activity using an atrial motion detector for use with, e.g., the illustrative systems and devices of FIGS. 1-5 and FIGS. 16-18.

FIG. 23 shows an illustrative method 600 of detecting atrial activity, for example, using the motion detector 11 of FIG. 2. In particular, method 600 may include detecting an atrial contraction based on analysis of a motion signal (e.g., provided by the motion detector 11) that may be performed by an IMD implanted in the patient's heart. In some embodiments, the motion signal may be provided by an IMD implanted within a ventricle, such as the right ventricle, of the patient's heart. The method 600 may include beginning an atrial contraction detection delay period upon identification of a ventricular activation event 630. The method 600 may include beginning an atrial contraction detection window upon expiration of the atrial contraction delay period 632. The method 600 may include analyzing the motion signal within the atrial contraction detection window.

The method 600 may include filtering the motion signal within the atrial contraction detection window, rectifying the filtered signal, and generating a derivative signal of the filtered and rectified motion signal within the atrial contraction detection window 634. The method 600 may include determining whether an amplitude of the derivative signal within the atrial contraction detection window exceeds a threshold 636. In response to determining that the amplitude of the derivative signal within the atrial contraction detection window exceeds the threshold (YES of 636), the method 600 may proceed to detecting atrial contraction 638. Otherwise (NO of 636), the method 600 may return to filtering, rectifying, and generating a derivative signal 634. Various techniques for using a motion detector that provides a motion signal may be described in U.S. Pat. No. 9,399,140 (Cho et al.), issued Jul. 26, 2016, entitled "Atrial contraction detection by a ventricular leadless pacing device for atriosynchronous ventricular pacing," which is incorporated herein by reference in its entirety.

Illustrative Embodiments

While the present disclosure is not so limited, an appreciation of various aspects of the disclosure of the present application will be gained through a discussion of some illustrative embodiments provided below.

Various illustrative embodiments are directed to atrioventricular synchronous pacing.

In illustrative embodiment 1, an implantable medical device includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The plurality of electrodes also includes a right atrial electrode positionable within the right atrium to at least one of deliver cardiac therapy and sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor electrical activity of the right atrium using the right atrial electrode and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity of the right atrium.

In illustrative embodiment 2, a method includes monitoring activity of the right atrium of a patient's heart using a right atrial electrode or a right atrial motion detector and delivering atrioventricular synchronous pacing using at least a tissue-piercing electrode implanted in the basal and/or septal region of the left ventricular myocardium of the patient's heart from the triangle of Koch region of the right atrium through the right atrial endocardium and central fibrous body including pacing one or both ventricles using at least the tissue-piercing electrode based on the monitored activity of the right atrium.

In illustrative embodiment 3, a device or method of any preceding illustrative embodiment is included, wherein delivering atrioventricular synchronous pacing includes using the right atrial electrode to pace the right atrium.

In illustrative embodiment 4, a device or method of any preceding illustrative embodiment is included, wherein delivering atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity of the right atrium includes sensing an atrial event within the monitored electrical activity of the right atrium and delivering a pace to one or both ventricles in response to the sensed atrial event.

In illustrative embodiment 5, a device or method of illustrative embodiment 4 is included, wherein delivering the pace to one or both ventricles in response to the sensed atrial event includes delivering the pace to one or both ventricles after a selected A-V time period has elapsed from the sensed atrial event.

In illustrative embodiment 6, a device or method of any preceding illustrative embodiment is included, wherein the controller is further configured to perform, or the method further includes, monitoring electrical activity of the left ventricle in the basal and/or septal region of the left ventricular myocardium using the tissue-piercing electrode implanted in the basal and/or septal region of the left ventricular myocardium of the patient's heart from the triangle of Koch region of the right atrium through the right atrial endocardium and central fibrous body; sensing a ventricular event within the monitored electrical activity from using the tissue-piercing electrode; and withholding delivering the pace to one or both ventricles in response to sensing the ventricular event within the monitored electrical activity from using the tissue-piercing electrode.

In illustrative embodiment 7, a device or method of any preceding illustrative embodiment is included, wherein the controller is further configured to perform, or the method further includes, detecting atrial fibrillation and initiating a single chamber pacing mode.

In illustrative embodiment 8, a device or method of any preceding illustrative embodiment is included, wherein the controller is further configured to perform, or the method further includes, receiving a trigger from a separate medical device in a triggered pacing mode.

In illustrative embodiment 8, a device or method of any preceding illustrative embodiment is included, wherein the controller is further configured to perform, or the method further includes, delivering pacing in an asynchronous pacing mode.

In illustrative embodiment 9, a device of any preceding illustrative embodiment is included, further including a housing extending from a proximal end region to a distal end region. The right atrial electrode is leadlessly coupled to the housing and the tissue-piercing electrode is leadlessly coupled to the distal end region of the housing. The therapy delivery circuit, the sensing circuit, and the controller are located within the housing.

In illustrative embodiment 10, the device of illustrative embodiment 9 is included, further including a fixation member that extends from the housing. The fixation member is configured to pierce into the myocardium. The fixation member extends from the distal end region of the housing toward a distal tip of the tissue-piercing electrode.

In illustrative embodiment 11, a device of any preceding illustrative embodiment is included, further including a housing, wherein the therapy delivery circuit, the sensing circuit, and the controller are located within the housing. The device further includes a lead coupled to and extending from the housing to a distal end region. The tissue-piercing electrode and the right atrial electrode are coupled to the distal end region of the lead.

In illustrative embodiment 12, a device of any preceding illustrative embodiment is included, further including a housing, wherein the therapy delivery circuit, the sensing circuit, and the controller are located within the housing. The device further includes a first lead coupled to and extending from the housing to a first distal end region and a second lead coupled to and extending from the housing to a second distal end region. The tissue-piercing electrode is coupled to the first distal end region of the first lead. The right atrial electrode is coupled to the second distal end region of the second lead.

In illustrative embodiment 13, a device of any preceding illustrative embodiment is included, further including a housing, wherein the therapy delivery circuit, the sensing circuit, and the controller are located within the housing. The device further includes a first lead coupled to and extending from the housing to a first distal end region, a second lead coupled to and extending from the housing to a second distal end region, and a third lead coupled to and extending from the housing to a third distal end region. The plurality of electrodes further includes a right ventricular electrode to deliver cardiac therapy to or sense electrical activity of the right ventricle of the patient's heart coupled to the third distal end region of the third lead. The tissue-piercing electrode is coupled to the first distal end region of the first lead. The right atrial electrode is coupled to the second distal end region of the second lead.

In illustrative embodiment 14, an implantable medical device includes a housing extending from a proximal end region to a distal end region. The device also includes a plurality of electrodes. The plurality of electrodes includes a tissue-piercing electrode leadlessly coupled to the distal end region of the housing and implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode leadlessly coupled to the housing and positionable within the right atrium to deliver cardiac therapy to or sense electrical activity of the right atrium of the patient's heart. The implantable medical device also includes a therapy delivery circuit within the housing operably coupled to the plurality of electrodes to deliver cardiac therapy to the patient's heart and a sensing circuit within the housing operably coupled to the plurality of electrodes to sense electrical activity of the patient's heart. The implantable medical device further includes a controller including processing circuitry within the housing operably coupled to the therapy delivery circuit and the sensing circuit. The controller is configured to monitor electrical activity of the right atrium using the right atrial electrode and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity of the right atrium.

In illustrative embodiment 15, an implantable medical device includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The tissue-piercing electrode also includes a right atrial motion detector positionable within the right atrium to sense mechanical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor mechanical activity of the right atrium using the right atrial motion detector and deliver atrioventricular synchronous pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored mechanical activity of the right atrium.

Various illustrative embodiments are directed to cardiac resynchronization pacing.

In illustrative embodiment 16, an implantable medical device includes a plurality of electrodes. The plurality of electrodes includes a tissue-piercing electrode implantable from the triangle of Koch region of the right atrium through the right atrial endocardium and central fibrous body to at least one of deliver cardiac therapy to or sense electrical activity of the left ventricle in the basal and/or septal region of the left ventricular myocardium of a patient's heart. The plurality of electrodes also includes a right atrial electrode positionable within the right atrium to at least one of deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor at least one of electrical activity of the right atrium using the right atrial electrode and electrical activity of the left ventricle using the tissue-piercing electrode implanted in the basal and/or septal region of the left ventricular myocardium of the patient's heart from the triangle of Koch region of the right atrium through the right atrial endocardium and central fibrous body. The controller is also configured to deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity.

In illustrative embodiment 17, a method includes monitoring at least one of electrical activity of the right atrium of a patient's heart using a right atrial electrode and electrical activity of the left ventricle using a tissue-piercing electrode implanted in the basal and/or septal region of the left ventricular myocardium of the patient's heart from the triangle of Koch region of the right atrium through the right atrial endocardium and central fibrous body. The method also includes delivering cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body including pacing one or both ventricles based on the monitored electrical activity.

In illustrative embodiment 18, a device or method of any preceding illustrative embodiment is included, wherein the controller is further configured to perform, or the method further includes, monitoring far-field electrical activity of the right ventricle using the right atrial electrode.

In illustrative embodiment 19, a device or method of any illustrative embodiment 16-18 is included, wherein delivering cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity includes sensing an atrial event within the monitored electrical activity of the right atrium and delivering a pace to one or both ventricles in response to the sensed atrial event to provide cardiac resynchronization.

In illustrative embodiment 20, a device or method of any illustrative embodiment 16-19 is included, wherein delivering cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity includes sensing a ventricular event within the monitored electrical activity from using the tissue-piercing electrode and delivering a pace to one or both ventricles in response to the sensed ventricular event to provide cardiac resynchronization.

In illustrative embodiment 21, the device or method of illustrative embodiment 20 is included, wherein delivering a pace to one or both ventricles in response to the sensed ventricular event includes delivering the pace to one or both ventricles after a selected time period has elapsed from the sensed ventricular event.

In illustrative embodiment 22, a device or method of any illustrative embodiment 16-21 is included, wherein the controller is further configured to perform, or the method further includes, detecting atrial fibrillation and initiating a single chamber pacing mode.

In illustrative embodiment 23, a device or method of any illustrative embodiment 16-22 is included, wherein the controller is further configured to perform, or the method further includes, receiving a trigger from a separate medical device in a triggered pacing mode.

In illustrative embodiment 24, a device or method of any illustrative embodiment 16-23 is included, wherein the controller is further configured to perform, or the method further includes, delivering pacing in an asynchronous pacing mode.

In illustrative embodiment 25, a device of any illustrative embodiment 16-24 is included, further including a housing extending from a proximal end region to a distal end region. The right atrial electrode is leadlessly coupled to the housing and the tissue-piercing electrode is leadlessly coupled to the distal end region of the housing. The therapy delivery circuit, the sensing circuit, and the controller are located within the housing.

In illustrative embodiment 26, the device of illustrative embodiment 25 is included, further including a fixation member that extends from the housing. The fixation member is configured to pierce into the myocardium. The fixation member extends from the distal end region of the housing toward a distal tip of the tissue-piercing electrode.

In illustrative embodiment 27, a device of any illustrative embodiment 16-26 is included, further including a housing, wherein the therapy delivery circuit, the sensing circuit, and the controller are located within the housing. The device further includes a lead coupled to and extending from the housing to a distal end region. The tissue-piercing electrode and the right atrial electrode are coupled to the distal end region of the lead.

In illustrative embodiment 28, a device of any illustrative embodiment 16-27 is included, further including a housing, wherein the therapy delivery circuit, the sensing circuit, and the controller are located within the housing. The device further includes a first lead coupled to and extending from the housing to a first distal end region and a second lead coupled to and extending from the housing to a second distal end region. The tissue-piercing electrode is coupled to the first distal end region of the first lead. The right atrial electrode is coupled to the second distal end region of the second lead.

In illustrative embodiment 29, a device of any illustrative embodiment 16-28 is included, further including a housing, wherein the therapy delivery circuit, the sensing circuit, and the controller are located within the housing. The device further includes a first lead coupled to and extending from the housing to a first distal end region, a second lead coupled to and extending from the housing to a second distal end region, and a third lead coupled to and extending from the housing to a third distal end region. The plurality of electrodes further includes a right ventricular electrode to deliver cardiac therapy to or sense electrical activity of the right ventricle of the patient's heart coupled to the third distal end region of the third lead. The tissue-piercing electrode is coupled to the first distal end region of the first lead. The right atrial electrode is coupled to the second distal end region of the second lead.

In illustrative embodiment 30, an implantable medical device includes a housing extending from a proximal end region to a distal end region. The implantable medical device also includes a plurality of electrodes. The plurality of electrodes includes a tissue-piercing electrode leadlessly coupled to the distal end region of the housing and implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode leadlessly coupled to the housing and positionable within the right atrium to deliver cardiac therapy to or sense electrical activity of the right atrium of the patient's heart. The implantable medical device also includes a therapy delivery circuit within the housing operably coupled to the plurality of electrodes to deliver cardiac therapy to the patient's heart and a sensing circuit within the housing operably coupled to the plurality of electrodes to sense electrical activity of the patient's heart. The implantable medical device further includes a controller including processing circuitry within the housing operably coupled to the therapy delivery circuit and the sensing circuit. The controller is configured to monitor at least one of electrical activity of the right atrium using the right atrial electrode and electrical activity of the left ventricle using the tissue-piercing electrode in the basal and/or septal region of the left ventricular myocardium of the patient's heart from the triangle of Koch region of the right atrium through the right atrial endocardium and central fibrous body. The controller is further configured to deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored electrical activity.

In illustrative embodiment 31, an implantable medical device includes a plurality of electrodes. The plurality of electrodes includes a tissue-piercing electrode implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. The plurality of electrodes also includes a right atrial motion detector positionable within the right atrium to sense mechanical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to monitor mechanical activity of the right atrium using the right atrial motion detector and deliver cardiac resynchronization pacing using at least the tissue-piercing electrode implanted in the basal and/or septal region of the left ventricular myocardium of the patient's heart from the triangle of Koch region of the right atrium through the right atrial endocardium and central fibrous body to pace one or both ventricles based on the monitored mechanical activity of the right atrium.

Various illustrative embodiments are directed to tachycardia therapy.

In illustrative embodiment 32, an implantable medical device includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to: monitor electrical activity of the right atrium using the right atrial electrode; monitor electrical activity of the left ventricle using the tissue-piercing electrode implanted in the basal and/or septal region of the left ventricular myocardium of the patient's heart from the triangle of Koch region of the right atrium through the right atrial endocardium and central fibrous body to sense electrical activity of the left ventricle in the basal and/or septal region of the left ventricular myocardium; and deliver tachycardia therapy based on the monitored electrical activities of the right atrium and the left ventricle.

In illustrative embodiment 33, a method includes monitoring electrical activity of the right atrium of a patient's heart using a right atrial electrode; monitoring electrical activity of the left ventricle of the patient's heart using a tissue-piercing electrode implanted in the basal and/or septal region of the left ventricular myocardium of the patient's heart from the triangle of Koch region of the right atrium through the right atrial endocardium and central fibrous body to sense electrical activity of the left ventricle in the basal and/or septal region of the left ventricular myocardium; and deliver tachycardia therapy based on the monitored electrical activities of the right atrium and the left ventricle.

In illustrative embodiment 34, a device or method of any illustrative embodiment 32-33 is included, wherein the controller is further configured to perform, or the method further includes, delivering tachycardia therapy based on the monitored electrical activities of the right atrium and left ventricle includes delivering at least one of anti-tachycardia pacing therapy using the plurality of electrodes and shock therapy using a separate medical device.

In illustrative embodiment 35, a device or method of any illustrative embodiment 32-34 is included, wherein the controller is further configured to perform, or the method further includes, withholding tachycardia therapy in response to a determining that a cardiac rhythm of the patient's heart has 1:1 atrioventricular conduction.

In illustrative embodiment 36, a device of any illustrative embodiment 32-35 is included, further including a housing extending from a proximal end region to a distal end region, wherein the right atrial electrode is leadlessly coupled to the housing and the tissue-piercing electrode is leadlessly coupled to the distal end region of the housing, wherein the therapy delivery circuit, the sensing circuit, and the controller are enclosed within the housing.

In illustrative embodiment 37, the device of illustrative embodiment 36 is included, further including a fixation member that extends from the housing. The fixation member is configured to pierce into the myocardium. The fixation member extends from the distal end region of the housing toward a distal tip of the tissue-piercing electrode.

In illustrative embodiment 38, a device of any illustrative embodiment 32-37 is included, further including a housing, wherein the therapy delivery circuit, the sensing circuit, and the controller are located within the housing. The device further includes a lead coupled to and extending from the housing to a distal end region. The tissue-piercing electrode and the right atrial electrode are coupled to the distal end region of the lead.

In illustrative embodiment 39, a device of any illustrative embodiment 32-38 is included, further including a housing, wherein the therapy delivery circuit, the sensing circuit, and the controller are located within the housing. The device further includes a first lead coupled to and extending from the housing to a first distal end region and a second lead coupled to and extending from the housing to a second distal end region. The tissue-piercing electrode is coupled to the first distal end region of the first lead. The right atrial electrode is coupled to the second distal end region of the second lead.

In illustrative embodiment 40, a device of any illustrative embodiment 32-39 is included, further including a housing, wherein the therapy delivery circuit, the sensing circuit, and the controller are located within the housing. The device further includes a first lead coupled to and extending from the housing to a first distal end region, a second lead coupled to and extending from the housing to a second distal end region, and a third lead coupled to and extending from the housing to a third distal end region. The plurality of electrodes further includes a right ventricular electrode to deliver cardiac therapy to or sense electrical activity of the right ventricle of the patient's heart coupled to the third distal end region of the third lead. The tissue-piercing electrode is coupled to the first distal end region of the first lead. The right atrial electrode is coupled to the second distal end region of the second lead.

In illustrative embodiment 41, an implantable medical device includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to: monitor electrical activity of the right atrium using the right atrial electrode; monitor electrical activity of the left ventricle using the tissue-piercing electrode implanted to sense electrical activity of the left ventricle in the basal and/or septal region of the left ventricular myocardium of the patient's heart from the triangle of Koch region of the right atrium through the right atrial endocardium and central fibrous body; and determine tachycardia of the patient's heart based on the monitored electrical activities of the right atrium and the left ventricle.

In illustrative embodiment 42, a method includes monitoring electrical activity of the right atrium of a patient's heart using a right atrial electrode; monitoring electrical activity of the left ventricle of the patient's heart using a tissue-piercing electrode implanted to sense electrical activity of the left ventricle in the basal and/or septal region of the left ventricular myocardium of the patient's heart from the triangle of Koch region of the right atrium through the right atrial endocardium and central fibrous body; and determining tachycardia of the patient's heart based on the monitored electrical activities of the right atrium and the left ventricle.

In illustrative embodiment 43, a device or method of any illustrative embodiment 41-42 is included, wherein the controller is further configured to perform, or the method further includes, determining whether a cardiac rhythm of the patient's heart has 1:1 atrioventricular conduction.

In illustrative embodiment 44, a device or method of illustrative embodiment 43 is included, wherein the controller is further configured to perform, or the method further includes, determining appropriate tachycardia therapy based on the monitored electrical activities of the right atrium and the left ventricle in response to the cardiac rhythm not having 1:1 atrioventricular conduction.

In illustrative embodiment 45, a device or method of any illustrative embodiment 41-44 is included, wherein determining tachycardia of the patient's heart based on the monitored electrical activities of the right atrium and the left ventricle includes determining that an atrial rhythm is regular and that a ventricular rhythm exceeds a selected ventricular rhythm threshold.

In illustrative embodiment 46, a device or method of any illustrative embodiment 41-45 is included, wherein the controller is further configured to perform, or the method further includes, delivering tachycardia therapy in response to determining tachycardia of the patient's heart.

In illustrative embodiment 47, a device or method of illustrative embodiment 46 is included, wherein the controller is further configured to perform, or the method further includes, delivering anti-tachycardia pacing therapy in response to a regular V-V event interval and a regular electrogram morphology.

In illustrative embodiment 48, a device or method of any illustrative embodiment 46-47 is included, wherein the controller is further configured to perform, or the method further includes, delivering shock therapy using a separate medical device in response to at least one of an irregular V-V event interval and an irregular electrogram morphology.

In illustrative embodiment 49, an implantable medical device includes a plurality of electrodes. The plurality of electrodes includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. The plurality of electrodes also includes a right atrial electrode positionable within the right atrium to deliver cardiac therapy to or sense electrical activity of the right atrium of the patient's heart. The implantable medical device also includes a therapy delivery circuit operably coupled to the plurality of electrodes to deliver cardiac therapy to the patient's heart and a sensing circuit operably coupled to the plurality of electrodes to sense electrical activity of the patient's heart. The implantable medical device further includes a controller including processing circuitry operably coupled to the therapy delivery circuit and the sensing circuit. The controller is configured to deliver at least one of anti-tachycardia pacing therapy using the plurality of electrodes and shock therapy using a separate medical device.

In illustrative embodiment 50, a method includes delivering at least one of anti-tachycardia pacing therapy and shock therapy using a separate medical device using at least a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart.

In illustrative embodiment 51, a device or method of any illustrative embodiment 49-59 is included, wherein the controller is further configured to perform, or the method further includes, detecting whether a ventricular rhythm exceeds a selected ventricular rhythm threshold after beginning to deliver anti-tachycardia pacing therapy.

In illustrative embodiment 52, a device or method of any illustrative embodiment 49-51 is included, wherein the controller is further configured to perform, or the method further includes, monitoring for tachycardia in response to detecting a regular ventricular rhythm.

In illustrative embodiment 53, a device or method of any illustrative embodiment 49-52 is included, wherein the controller is further configured to perform, or the method further includes, delivering shock therapy using a separate device therapy in response to detecting a ventricular rhythm that exceeds the selected ventricular rhythm threshold.

In illustrative embodiment 54, a device or method of any illustrative embodiment 49-53 is included, wherein the shock therapy includes delivering a signaling pulse to the left ventricle using the tissue-piercing electrode.

In illustrative embodiment 55, a device or method of illustrative embodiment 54 is included, wherein the signaling pulse is configured to be detected by the separate medical device to trigger delivery of a shock from the separate medical device to the cardiac tissue.

In illustrative embodiment 56, a device or method of any illustrative embodiment 49-54 is included, wherein the separate medical device is not connected to the implantable medical device by a metal conductor.

Thus, various embodiments of VFA CARDIAC THERAPY are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

It will be understood that each block of the block diagrams and combinations of those blocks can be implemented by means for performing the illustrated function.

All references and publications cited herein are expressly incorporated herein by reference in their entirety into this disclosure, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, an intracardiac medical device may be operatively or operably coupled to an extravascular ICD to initiate shock therapy).

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A method comprising:
monitoring activity of the right atrium of a patient's heart using a right atrial electrode or a right atrial motion detector; and
delivering atrioventricular synchronous pacing using at least a tissue-piercing electrode implanted in a basal and/or septal region of the left ventricular myocardium of the patient's heart from the triangle of Koch region of the right atrium through the right atrial endocardium and the central fibrous body comprising pacing one or both ventricles using at least the tissue-piercing electrode based on the monitored activity of the right atrium.

2. The method according to claim 1, further comprising delivering the atrioventricular synchronous pacing to the right atrium using the right atrial electrode.

3. The method according to claim 1, wherein pacing the one or both ventricles using at least the tissue-piercing electrode based on the monitored electrical activity of the right atrium comprises: sensing an atrial event within the monitored electrical activity of the right atrium; and delivering a pace to the one or both ventricles in response to the sensed atrial event.

4. The method according to claim 3, wherein delivering the pace to the one or both ventricles in response to the sensed atrial event comprises delivering the pace to the one or both ventricles after a selected A-V time period has elapsed from the sensed atrial event.

5. The method according to claim 3, further comprising: monitoring electrical activity of the left ventricle in the basal and/or septal region of the left ventricular myocardium using the tissue-piercing electrode implanted in the basal and/or septal region of the left ventricular myocardium of the patient's heart from the triangle of Koch region of the right atrium through the right atrial endocardium and the central fibrous body;

sensing a ventricular event within the monitored electrical activity of the left ventricle from using the tissue-piercing electrode; and withholding delivery of the pace to the one or both ventricles in response to sensing the ventricular event within the monitored electrical activity of the left ventricle from using the tissue-piercing electrode.

\* \* \* \* \*